United States Patent
Maher et al.

(10) Patent No.: US 10,557,117 B2
(45) Date of Patent: Feb. 11, 2020

(54) GAMMADELTA T CELL EXPANSION PROCEDURE

(71) Applicant: KING'S COLLEGE LONDON, London (GB)

(72) Inventors: John Maher, London (GB); Ana Catarina Parente Pereira Puri, London (GB); Richard Esmond Beatson, London (GB)

(73) Assignee: King's College London, London (GB)

( * ) Notice: Subject to any disclaimer, the term of this patent is extended or adjusted under 35 U.S.C. 154(b) by 7 days.

(21) Appl. No.: 15/532,921

(22) PCT Filed: Dec. 4, 2015

(86) PCT No.: PCT/GB2015/053713
§ 371 (c)(1),
(2) Date: Jun. 2, 2017

(87) PCT Pub. No.: WO2016/087871
PCT Pub. Date: Jun. 9, 2016

(65) Prior Publication Data
US 2017/0342381 A1  Nov. 30, 2017

(30) Foreign Application Priority Data
Dec. 5, 2014 (GB) .................... 1421716.0

(51) Int. Cl.
*C12N 5/0783* (2010.01)
*A61K 35/17* (2015.01)
*A61K 31/7068* (2006.01)

(52) U.S. Cl.
CPC ........ *C12N 5/0636* (2013.01); *A61K 31/7068* (2013.01); *A61K 35/17* (2013.01); *C12N 2501/15* (2013.01); *C12N 2501/20* (2013.01); *C12N 2501/2302* (2013.01); *C12N 2501/999* (2013.01); *C12N 2506/11* (2013.01)

(58) Field of Classification Search
None
See application file for complete search history.

(56) References Cited

U.S. PATENT DOCUMENTS

| | | |
|---|---|---|
| 2005/0196385 A1 | 9/2005 | Romagne et al. |
| 2007/0134273 A1 | 6/2007 | Romagne et al. |
| 2007/0197436 A1 | 8/2007 | Thacker |
| 2013/0052160 A1 | 2/2013 | Zitvogel et al. |

FOREIGN PATENT DOCUMENTS

| | | |
|---|---|---|
| CN | 103436493 A | 12/2013 |
| WO | 98/49270 A1 | 11/1998 |
| WO | 2004050096 A2 | 6/2004 |
| WO | 2006/017954 A1 | 2/2006 |
| WO | 2009037723 A1 | 3/2009 |
| WO | 2014/172584 A1 | 10/2014 |
| WO | 2016/087871 A1 | 6/2016 |

OTHER PUBLICATIONS

Kondo et al., J. Vis. Exp. 55(e3182):1-6 (2011).*
Kreslavsky et al., Immunol. Rev., 238(1): 169-181 (2010).*
Capietto et al., J. Immunol., 184:6680-6687 (2010) (Year: 2010).*
Ramstead et al., "Complex Role of γδ T-Cell-Derived Cytokines and Growth Factors in Cancer", Journal of Interferon & Cytokine Research, 2012, pp. 563-569, vol. 32, No. 12.
Schilbach et al., "Immune Response of Human Propagated γδ-T-Cells to Neuroblastoma Recommend the Vδ1+ Subset for γδ-T-cell-based Immunotherapy", Journal of Immunotherapy 2008, pp. 896-905, vol. 31, No. 9.
Su et al., "Tc-methylene diphosphonate improves rheumatoid arthritis disease activity by increasing the frequency of peripheral γδ T cells and CD4+CD25+Foxp3+Tregs", International Journal of Rheumatic Diseases, Jan. 28, 2014, 18 pgs.
Sutton et al., "Interleukin-1 and IL-23 Induce Innate IL-17 Production from γδ T Cells, Amplifying Th17 Responses and Autoimmunity", Immunity, 2009, pp. 331-341, vol. 31.
Suzuki et al., "Regulatory Role of γδ T Cells in Uterine Intraepithelial Lymphocytes in Maternal Antifetal Immune Response", The Journal of Immunology, 1995, pp. 4476-4484, vol. 154.
Thomas et al., "TGF-β directly targets cytotoxic T cell functions during tumor evasion of immune surveillance", Cancer Cell, 2005, pp. 369-380, vol. 8.
Tiemessen et al., "Transforming growth factor-β inhibits human antigen-specific CD4+ T cell proliferation without modulating the cytokine response", International Immunology, 2003, pp. 1495-1504, vol. 15, No. 12.
Vantourout et al., "Six-of-the-best: unique contributions of γδ T cells to immunology", Nat Rev Immunol, 2013, pp. 88-100, vol. 13, No. 2.
Vantourout et al., "Immunological Visibility: Posttranscriptional Regulation of Human NKG2D Ligands by the EGF Receptor Pathway", Science Translational Medicine, 2014, 231ra49, 14 pgs., vol. 6.
Visperas et al., "γδ T cells restrain extrathymic development of Foxp3+-inducible regulatory T cells via IFN-γ", European Journal of Immunology, 2014, pp. 2448-2456, vol. 44, No. 8.
Vlasselaer et al., "Transforming Growth Factor-β Directs IgA Switching in Human B Cells", The Journal of Immunology, 1992, pp. 2062-2067, vol. 148.
Wakita et al., "Tumor-infiltrating IL-17-producing γδ T cells support the progression of tumor by promoting angiogenesis", European Journal of Immunology, 2010, pp. 1927-1937, vol. 40.
Wilhelm et al., "Successful adoptive transfer and in vivo expansion of haploidentical γδ T cells", Journal of Translational Medicine, 2014, 5 pgs., vol. 12, No. 45.

(Continued)

*Primary Examiner* — Thomas J. Visone

(57) ABSTRACT

A method for expanding a population of γδ T-cells is provided in which isolated activated Peripheral Blood Mononuclear Cells (PBMCs) are cultured in a medium comprising transforming growth factor beta (TGF-β) under conditions in which the production of effector γδ T-cells having therapeutic activity against malignant disease is favored. The use of TGF-β in the production of effector cells in particular Vγ9Vδ2 T-cells is also described and claimed.

16 Claims, 34 Drawing Sheets

(56) References Cited

OTHER PUBLICATIONS

Workalemahu et al., "Human γδ-T Lymphocytes Express and Synthesize Connective Tissue Growth Factor: Effect of IL-15 and TGF-β1 and Comparison with αβ-T Lymphocytes", The Journal of Immunology, 2003, pp. 153-157, vol. 170.
Workalemahu et al., "Expression and synthesis of fibroblast growth factor-9 in human γδ T-lymphocytes. Response to isopentenyl pyrophosphate and TGF-β1/IL-15", Journal of Leukocyte Biology, 2004, pp. 657-663, vol. 75.
Workalemahu et al., "Expression of Metalloproteinase-7 (Matrilysin) in Human Blood and Bronchoalveolar Gamma/Delta T-Lymphocytes. Selective Upregulation by the Soluble Non-Peptidic Mycobacterial Phosphoantigen (Isopentenyl Pyrophosphate)", Journal of Cellular Physiology, 2006, pp. 67-74, vol. 207.
Worku et al., "Differential Effects of Control and Antigen-Specific T Cells on Intracellular Mycobacterial Growth", Infection and Immunity, 2003, pp. 1763-1773, vol. 71, No. 4.
Yu et al., "Expansion and Immunological Study of Human Tumor Infiltrating Gamma/Delta T Lymphocytes in vitro", International Archives of Allergy and Immunology, 1999, pp. 31-37, vol. 119.
Agea et al., "Human CD1-restricted T cell recognition of lipids from pollens", The Journal of Experimental Medicine, 2005, pp. 295-308, vol. 202, No. 2.
Beagley et al., "The Mycobacterium tuberculosis 71-kDa heat-shock protein induces proliferation and cytokine secretion by murine gut intraepithelial lymphocytes", European Journal of Immunology, 1993, pp. 2049-2052, vol. 23.
Bennouna et al., "Phase-I study of Innacell γδ™, an autologous cell-therapy product highly enriched in γ9δ2 T lymphocytes, in combination with IL-2, in patients with metastatic renal cell carcinoma", Cancer Immunol Immunother, 2008, pp. 1599-1609, vol. 57.
Benzaid et al., "High Phosphoantigen Levels in Bisphosphonate-Treated Human Breast Tumors Promote V γ9Vδ2 T-Cell Chemotaxis and Cytotoxicity In Vivo", Cancer Research, 2011, pp. 4562-4572, vol. 71, No. 13.
Benzaid et al., "In Vivo Phosphoantigen Levels in Bisphosphonate-Treated Human Breast Tumors Trigger V γ9Vδ2 T-cell Antitumor Cytotoxicity through ICAM-1 Engagement", Clinical Cancer Research, 2012, pp. 6249-6259, vol. 18, No. 22.
Brandes et al., "Professional Antigen-Presentation Function by Human γδ T Cells", Science, 2005, pp. 264-268, vol. 309, No. 5732.
Caccamo et al., "Differentiation, phenotype, and function of interleukin-17-producing human V γ9Vδ2 T cells", Blood, 2011, pp. 129-138, vol. 118, No. 1.
Capietto et al., "Phosphoantigens Overcome Human TCRVγ9+ γδ Cell Immunosuppression by TGF-β: Relevance for Cancer Immunotherapy", The Journal of Immunology, 2010, pp. 6680-6687, vol. 184.
Casetti et al. "Cutting Edge: TGF-β1 and IL-15 Induce FOXP3+ γδ Regulatory T Cells in the Presence of Antigen Stimulation", The Journal of Immunology, 2009, pp. 3574-3577, vol. 183.
Clendening et al., "Dysregulation of the mevalonate pathway promotes transformation", PNAS, 2010, pp. 15051-15056, vol. 107, No. 34.
Deniger et al., "Activating and Propagating Polyclonal Gamma Delta T Cells with Broad Specificity for Malignancies", Clinical Cancer Research, 2014, pp. 5708-5719, vol. 20, No. 22.
Dieli et al., "Targeting Human γδ T Cells with Zoledronate and Interleukin-2 for Immunotherapy of Hormone-Refractory Prostate Cancer", Cancer Research, 2007, pp. 7450-7457, vol. 67.
Do et al., "Cutting Edge: Spontaneous Development of IL-17-Producing γδ T Cells in the Thymus Occurs via a TGF-β1-Dependent Mechanism", The Journal of Immunology, 2010, pp. 1675-1679, vol. 184.
Dunford et al., "Structure-Activity Relationships Among the Nitrogen Containing Bisphosphonates in Clinical Use and Other Analogues: Time-Dependent Inhibition of Human Farnesyl Pyrophosphate Synthase", Journal of Medicinal Chemistry, 2008, pp. 2187-2195, vol. 51, No. 7.
Ersvaer et al., "Effects of cytarabine on activation of human T cells—cytarabine has concentration-dependent affects that are modulated both by valproic acid and all-trans retinoic acid", BMC Pharmacology & Toxicology, 2015, pp. 1-16, vol. 16, No. 12.
Fan et al., "The decidual gamma-delta T cells up-regulate the biological functions of trophoblasts via IL-10 secretion in early human pregnancy", Clinical Immunology, 2011, pp. 284-292, vol. 141.
Fisher et al., "γδ T cells for cancer immunotherapy, A systematic review of clinical trials", OncoImmunology, 2014, pp. e27572-1-e27572-10, vol. 3.
Giacomelli et al "γ/δ T cells in placenta and skin: Their different functions may support the paradigm of microchimerism systemic sclerosis", Clin Exp Rheumatol, 2004, pp. S-28-S30, vol. 22.
Goodier et al., "Cytokine profiles for human Vγ9+ T cells stimulated by Plasmodium falciparum", Parasite Immunology, 1995, pp. 413-423, vol. 17, No. 8.
Gorczynski et al., "Evidence for Persistent Expression of OX2 as a Necessary Component of Prolonged Renal Allograft Survival Following Portal Vein Immunization", Clinical Immunology, 2000, pp. 69-78, vol. 97, No. 1.
Gu et al., "Rapamycin together with TGF-β1, IL-2 and IL-15 induces the generation of functional regulatory γδT cells from human peripheral blood mononuclear cells", Journal of Immunological Methods, 2014, pp. 82-87, vol. 402.
Guzman et al., "Bovine γδ T Cells Are a Major Regulatory T Cell Subset", The Journal of Immunology, 2014, pp. 208-222, vol. 193, No. 1.
Haury et al., "Intestinal T lymphocytes in the chicken express an integrin-like antigen", European Journal of Immunology, 1993, pp. 313-319, vol. 23.
Hostettler et al., "Dissecting the Dualistic Effects of Transforming Growth Factor (TGF)-β on Fibroproliferation and Extracellular Matrix Production in Primary Human Lung Fibroblasts—The Role of P38δ Map Kinase", The Open Critical Care Medicine Journal, 2009, pp. 28-37, vol. 2.
Inagaki-Ohara et al., "Mucosal T Cells Bearing TCRγδ Play a Protective Role in Intestinal Inflammation", The Journal of Immunology, 2004, pp. 1390-1398, vol. 173.
International Search Report and Written Opinion from related International Application No. PCT/GB2015/053713, dated Apr. 15, 2016; 20 pgs.
Kang et al., "Identification and characterization of Foxp3+ γδ T cells in mouse and human", Immunology Letters, 2009, pp. 105-113, vol. 125.
Kobayashi et al., "Complete Remission of Lung Metastasis Following Adoptive Immunotherapy Using Activated Autologous γδ T-cells in a Patient with Renal Cell Carcinoma", Anticancer Research, 2010, pp. 575-579, vol. 30.
Kondo et al., "Zoledronate facilitates large-scale ex vivo expansion of functional γδ T cells from cancer patients for use in adoptive immunotherapy", Cytotherapy, 2008, pp. 842-856, vol. 10, No. 8.
Kuhl et al., "Human peripheral γδ T cells possess regulatory potential", Immunology, 2009, pp. 580-588, vol. 128.
Laggner et al., "Regression of melanoma metastases following treatment with the n-bisphosphonate zoledronate and localised radiotherapy", Clinical Immunology, 2009, pp. 367-373, vol. 131.
Lei et al., "Peroxisome Proliferator-Activated Receptor α and γ Agonists Together with TGF-β Convert Human CD4+CD25- T Cells into Functional Foxp3+ Regulatory T Cells", The Journal of Immunology, 2010, pp. 7186-7198, vol. 185.
Li et al., "Generation of Human Regulatory γδ T Cells by TCRγδ Stimulation in the Presence of TGF-β and Their Involvement in the Pathogenesis of Systemic Lupus Erythematosus", The Journal of Immunology, 2011, pp. 6693-6700, vol. 186.
Mattarollo et al. "Chemotherapy and zoledronate sensitize solid tumour cells to Vγ9Vδ2 T cell cytotoxicity", Cancer Immunology and Immunotherapy, 2007, 14 pgs.

(56) References Cited

OTHER PUBLICATIONS

Mincheva-Nilsson, "Pregnancy and gamma/delta T cells: Taking on the hard questions", Reproductive Biology and Endocrinology, 2003, 11 pgs., vol. 1.

Mohammed et al., "TGFβ1-Induced Inflammation in Premalignant Epidermal Squamous Lesions Requires IL-17", Journal of Investigative Dermatology, 2010, pp. 2295-2303, vol. 130.

Nagaeva et al., "Dominant IL-10 and TGF-β mRNA Expression in δ2T Cells of Human Early Pregnancy Decidua Suggests Immunoregulatory Potential", American Journal of Reproductive Immunology, 2002, pp. 9-17, vol. 48.

Nantz et al., "Immunity and Antioxidant Capacity in Humans Is Enhanced by Consumption of a Dried, Encapsulated Fruit and Vegetable Juice Concentrate", The Journal of Nutrition, 2006, pp. 2606-2610, vol. 136.

Ness-Schwickerath et al., "Regulation and function of IL-17A- and IL-22-producing γδ T cells", Cell Mol Life Sci., 2011, pp. 2371-2390, vol. 68, No. 14.

Nicol et al., "Clinical evaluation of autologous gamma delta T cell-based immunotherapy for metastatic solid tumours", British Journal of Cancer, 2011, pp. 778-786, vol. 105, No. 6.

Okragly et al., "Monocytes control γ/δ T-cell responses by a secreted product", Immunology, 1995, pp. 599-605, vol. 86.

Parente-Pereira et al., "Use of retroviral-mediated gene transfer to deliver and test function of chimeric antigen receptors in human T-cells", Journal of Biological Methods, 2014, e7, pp. 1-9, vol. 1, No. 2.

Parente-Pereira et al., "Adoptive Immunotherapy of Epithelial Ovarian Cancer with Vγ9Vδ2 T Cells, Potentiated by Liposomal Alendronic Acid", The Journal of Immunology, 2014, pp. 5557-5566, vol. 193.

Quatromoni et al., "The timing of TGF-β inhibition affects the generation of antigen-specific CD8+ T Cells", BMC Immunology, 2013, 16 pgs., vol. 14, No. 30.

Quere et al., "Multiple Suppressive Effects of Transforming Growth Factor β1 on the Immune Response in Chickens", Cellular Immunology, 1990, pp. 468-477, vol. 129.

Patent Search Report related to Russian Application No. RU2017121191; 4 pgs.

\* cited by examiner

GAMMADELTA T CELL EXPANSION PROCEDURE

The present invention relates to methods for the expansion of γδ T-cells in particular human Vγ9Vδ2T-cells having anti-tumor effector function, as well as to reagents and compositions for use in the methods, and the products of the methods and their use in therapy. In addition, the methods are suitable for enhancing cell expansion efficiency and effector function in some instances.

BACKGROUND TO THE INVENTION

γδ T-cells account for up to 10% of circulating lymphocytes and operate at the interface between innate and adaptive immunity. Four attributes of these versatile cells render them ripe for exploitation in therapies and in particular in cancer immunotherapy. First, γδ T-cells recognise genomic, metabolic and signaling perturbations associated with the transformed state [1, 2]. Second, they possess a diverse network of immune effector activities, overlapping and yet distinct to those deployed by "conventional" αβ T-cells. γδ T-cells release perforin and granzymes, express both FAS and TRAIL, engage in Fc receptor-dependent effector functions and produce a range of immunomodulatory cytokines, including tumor necrosis factor (TNF)-α, interferon (IFN)-γ and IL-17. Third, γδ T-cells act as efficient antigen-presenting cells, enabling the perpetuation of immune attack through adaptive mechanisms [3]. Finally, since these cells are not HLA-restricted, they do not elicit graft versus host disease. This enhances the prospect of their future use in the allogeneic "off the shelf" setting [4].

Most circulating γδ T-cells in man display a Vγ9Vδ2 receptor that recognises non-peptide phosphoantigens (PAgs), best exemplified by IPP and its stereoisomer DMAPP (FIG. 1) [5]. Since PAgs are intermediates of mevalonate metabolism, Vγ9Vδ2 T-cells provide an innate mechanism to detect excess activity of this key metabolic pathway. Such surveillance is justified from an evolutionary standpoint since excess mevalonate pathway flux promotes cellular transformation, acting synergistically with p21Ras [6]. This reflects the fundamental role of this network in the biosynthesis of isoprenoids required for post-translational modification of several GTPases, including p21Ras, Cdc42, Rho, Rab and Rac.

Amino-bisphosphonate (NBP) drugs such as zoledronic (ZA), alendronic (AA), pamidronic (PA) and ibandronic acid (IA) exert anti-tumor activity through a combination of directly cytotoxic and immunomodulatory mechanisms [7]. A key example of the latter is the ability of these drugs to activate Vγ9Vδ2 T-cells. This results from inhibition of FPP synthase within the mevalonate pathway, leading to increased PAg accumulation (FIG. 1) [8]. Tumor cells that have been pulsed with NBPs rapidly acquire large PAg loads and thus become more sensitive to recognition by Vγ9Vδ2 T-cells [5, 9]. Exploitation of this principle provides an opportunity to enhance tumor susceptibility to γδ T-cell immunotherapy.

The clinical development of γδ T-cell immunotherapy builds on two established findings. First, in an effort to achieve in-vivo expansion of Vγ9Vδ2 T-cells, patients with diverse malignancies have been treated with ZA and low-dose IL-2. In many cases, these small studies have correlated circulating Vγ9Vδ2 T-cell numbers with retarded disease progression [10]. Second, ex-vivo expanded Vγ9Vδ2 T-cells have been tested as an autologous adoptive immunotherapy in several early phase clinical trials, involving diverse cancers including epithelial ovarian cancer (EOC) [11-13]. Although these studies have demonstrated the safety of infused γδ T-cells, clinical efficacy has been limited (even when combined with ZA). This highlights the need for better systems to expand these cells at high efficiency, yielding cells that exhibit improved anti-tumor activity.

Transforming growth factor-β (TGF-β) is a secreted protein that exists in at least three isoforms, called TGF-β1, TGF-β2 and TGF-β3. It is a cytokine that has a role in a variety of processes including proliferation and cellular differentiation, but also immunity and cancer. It is generally understood that in this context, it has a regulatory immune effect, and this may explain in part why it is upregulated in certain cancers, which overexpress the cytokine to reduce the host immune response. There are many papers showing that addition of TGF-β to T-cells promotes a regulatory phenotype. For example, two independent groups have shown that culturing human peripheral blood mononuclear cells (PBMCs) in the presence of cytokines that included TGF-β resulted in the production of regulatory γδ T-cells expressing high levels of Foxp3 and CD25 having an immunosuppressive function [14, 15].

The applicants have carried out studies of various protocols for the expansion of γδ T-cells and have found a particular set of conditions which produce high levels of cells with enhanced effector activity.

SUMMARY OF THE INVENTION

Surprisingly, the applicants have found that the presence of TGF-β can, under certain culture conditions, produce enhanced yields of effector T-cells having an immunostimulatory activity, in particular against cancer cells. Furthermore, the anti-cancer efficacy of the cells produced using this method may be increased.

According to the present invention there is provided a method for expanding a population of γδ T-cells, said method comprising culturing isolated activated peripheral blood mononuclear cells (PBMCs) in a medium comprising transforming growth factor beta (TGF-β) under conditions in which the production of effector γδ T-cells having therapeutic activity against malignant disease is favored.

In particular, the T-cell population produced using the method of the invention is rich in γδ cells and in particular Vγ9Vδ2 cells, having therapeutic activity against malignant disease. Malignant disease in this case includes in particular proliferative disease such as cancer, including solid tumors, liquid tumors or blood cancers or other cancers of the circulatory system. Examples of solid tumors include breast cancer, ovarian cancer, cancer of the colon and generally the GI (gastro-intestinal) tract, cervix cancer, lung cancer, in particular small-cell lung cancer, and non-small-cell lung cancer, head and neck cancer, bladder cancer, cancer of the prostate or Kaposi's sarcoma. Examples of circulatory system cancers include leukemias such as Acute Myeloid leukaemia (AML), Myelo-dysplastic syndrome (MDS), myelo-proliferative diseases (MPD), Chronic Myeloid Leukemia (CML) T-cell Acute Lymphoblastic leukaemia (T-ALL), B-cell Acute Lymphoblastic leukemia (B-ALL), Non-Hodgkins Lymphoma (NHL) and B-cell lymphoma.

As used herein, the expression 'effector T-cells' refers to T-cells having an anti-tumor or anti-leukemic effect rather than a regulatory or immunosuppressive effect on the immune response.

It appears that by including TGF-β in the culture medium under certain conditions, both the yield and efficacy of the effector T-cells is increased. This runs contrary to the prevailing understanding that this cytokine results in the production of principally regulatory T-cells.

The PBMCs used as the starting material in the process of the invention are suitably primate PBMCs such as human PBMCs. They are suitably isolated from blood samples from humans or other primates such as apes, using conventional methods.

The cells may be obtained from a patient and then reintroduced into that patient (autologous therapy). However, in some circumstances, it has been found that cells from patients who have been heavily pre-treated, for example for solid tumors such as triple negative breast cancer, expand poorly or not at all. In such cases, it may be necessary to obtain the PBMCs used as the starting material in the method of the invention from a healthy donor and to adopt an allogeneic approach to the therapy. In this case, it would be advisable to purify γδ T cells from the expanded product, in particular to remove potentially hazardous B-cells (CD19$^+$) and αβ T-cells, in order to facilitate the safe allogeneic use of the γδ T cells.

The TGF-β is suitably present in the culture medium at a concentration of from 0.1-100 ng/mL, for example at a concentration of about 5 ng/mL. However the precise amount of TGF-β added may depend upon the biological activity of the TGF-β used. This may be determined using a suitable bioassay which yields an ED50 value, equivalent to a Unit of activity. For example, an ED50 for TGF-β may be determined by TGF-β's ability to inhibit the mouse IL-4-dependent proliferation of mouse HT-2 cells. Typically a concentration of 5 ng/ml equates to a specific activity of $2 \times 10^5$ units. Thus suitably from $4 \times 10^3$ to $4 \times 10^6$ units of TGF-β are added to the culture medium, where the unit is determined as described above.

The applicants have found that the nature of the medium may be important in this context. In particular, the medium employed by the applicants has been produced under good manufacturing process (GMP) and does not contain fetal calf serum or fetal bovine serum, which is frequently included in conventional T-cell culture media [14, 15 (personal communication, Dr Rita Casetti)]. These particular attributes of the culture medium appear to impact on the development of T-cells in the presence of TGF-β, favoring expansion of effector cells with anti-tumor activity in preference to regulatory T-cells.

In particular, the medium comprises a serum-free medium, such as a synthetic medium like TexMACS (Miltenyi) or RPMI and may be conducted in the additional presence of human AB serum. The medium is suitably a GMP grade medium.

Furthermore, the medium used may further comprise interleukin-2 (IL-2). Additional cytokines may be present provided they do not change the nature of the product as being predominantly effector type T-cells with anti-tumor and anti-leukemic activity. However, in a particular embodiment, the medium does not contain any additional cytokines.

Interleukin-2 is suitably present in the medium in an amount of from 1-1000 U/mL, for example at about 100 U/mL, where the U is units. One Unit of IL-2 in this context may be defined as the amount of IL-2 in 1 ml that will induce IL-2-dependent murine T cells to incorporate $^3$H-TdR at 50% of their maximum level after 24 hours of incubation.

The TGF-β as well as the IL-2 where present is suitably added repeatedly at intervals during the culture process, in particular in response to the cell expansion, which is suitably monitored throughout by counting cells.

The cells used as a starting material are activated. In a particular embodiment, this may be achieved by adding an activator capable of activating particularly Vγ9Vδ2 T-cells. Suitable activators may include amino-bisphosphonate drugs such as zoledronic (ZA), alendronic (AA), pamidronic (PA) and ibandronic acid (IA). In a particular embodiment, the activator is Zoledronic acid or a salt thereof. Alternatively cells may be activated using a phosphoantigen such as BRHPP or IPP.

The activator is suitably added in an effective amount. Addition may take place with the first addition of TGF-β and IL-2 where present. The concentration of activator added will depend upon factors such as the specific type of activator used, but will typically be in the range of from 0.1-10 μg/ml, for example at about 1 μg/ml.

After expansion as described above, γδ T-cells may then be obtained by purification of the expanded product. In particular, the CD19 and αβ T-cells may be removed from the product by negative selection or by use of suitable isolation techniques or kits. The applicants have found that if γδ T-cells are isolated from PBMCs prior to expansion, the expansion process may be ineffective.

Using the methods described above, the yield of effector T-cells expanded in-vitro can be enhanced, and so application of this method for enhancing T-cell expansion yield forms a further aspect of the invention.

Similarly, as described below, the efficacy and in particular the anti-cancer efficacy of the T-cells obtained using this method is enhanced. As a result, the invention further provides a method for enhancing the anti-cancer efficacy of T-cells expanded in-vitro by use of the expansion method described above.

Yet a further aspect of the invention provides the use of TGF-β for enhancing expansion of effector T-cells, and in particular human Vγ9Vδ2 T-cells which are useful in the treatment of malignant disease as described above.

In a further aspect, the invention provides the use of TGFβ for enhancing the anti-cancer effector ability of T-cells.

T-cells obtained by a method as described above form a further aspect of the invention. These may be used in therapy and in particular in for the treatment of cancer.

The cells may be used in the treatment of patients in a conventional manner. In particular, the invention also provides a method for treating a patient in need thereof by administration of T-cells obtained as described above. In particular the T-cells are adoptively transferred into patients in accordance with standard clinical practice.

In particular, the cells may be administered in conjunction with an activator such as those described herein and/or a chemotherapeutic agent. Suitable activators include bisphosphonate drugs such as zoledronic acid, alendronic acid and pamidronic acid. They may activate the T cells and also sensitize tumor to T-cells.

Certain chemotherapeutic agents have also been found to sensitize tumors to γδ T-cells [18] and thus these may also be pre- or co-administered with the γδ T-cells of the invention. Particular examples of such chemotherapeutic acids include cisplatin, etoposide, anthracyclines and, as illustrated hereinafter, cytarabine.

The applicants are the first to sequentially administer cytarabine followed by γδ T-cells to produce an anti-tumor effect and this novel therapy forms a further aspect of the invention. In this therapy, effective amounts of γδ T-cells and cytarabine are administered to a patient in need thereof. In particular, the γδ T-cells are obtained in accordance with the present invention.

It may be desirable also to co-administer a cytokine such as IL-2, in order to extend survival of the T-cells.

DETAILED DESCRIPTION OF THE INVENTION

The invention will now be particularly described by way of example with reference to the accompanying Figures.

BRIEF DESCRIPTION OF THE DRAWINGS

FIG. 4(A) IGROV-1; FIG. 4(B) KOC7C; FIG. 4(C) PEO1; FIG. 4(D) PEA; FIG. 4(E) SKOV-3; FIG. 4(F) TOV-21G.

FIG. 5A shows enrichment of Vγ9Vδ2 T-cells (mean±SEM, n=13 independent replicates). FIG. 5B shows expansion of Vγ9Vδ2 T-cells (mean±SEM, n=13 independent replicates). Percentage γδ T-cells present at the beginning and end of manufacture are also shown (mean±SD, n=10). *p=0.03 by Mann Whitney test.

FIG. 8(A) Method 2 expanded cells express a distinct immunophenotype with higher levels of memory (CD45RO, CD27) and homing receptors (CCR7, CXCR4, cutaneous leukocyte antigen (CLA) and E-selectin binding receptors (detected using E-selectin-IgG fusion protein—FIG. 8B). FIG. 8(C) Relative (rel.) to method, 1, the proportion of naïve (CD45RA$^+$ CCR7$^+$) and central memory (CD45$^-$ CD27$^+$) cells was higher in method 2-expanded cells. NS—not significant; *p<0.05; p<0.01; *p<0.001; ****p<0.0001.

FIG. 11(A) shows tumor burden, indicated by bioluminescence; and FIG. 11(B) shows the weight of mice, providing an indication of toxicity of the treatment.

FIG. 12(A) Tumor burden, indicated by bioluminescence. FIG. 12(B) Survival of mice. FIG. 12(C) Weight of mice, providing an indication of toxicity of the treatment.

FIG. 13(A) illustrates how Vγ9Vδ2 T-cells were purified from freshly isolated PBMC by negative selection using a CD19 and αβ T-cell microbead isolation kit; FIG. 13(B) shows the results of attempts to expand these cells; FIG. 13(C) shows the % cell type obtained in experiments in which γδ T-cells were expanded from PBMC using the method of the invention prior to subsequent depletion of CD19 and αβ T-cells by negative selection; FIG. 13(D) shows the results of flow cytometry analysis of these cells following depletion of contaminating CD19 and αβ T-cells; FIG. 13(E) shows the results of a 24 hour cytotoxicity test of the cells (5:1 effector:target ratio) against MDA-MB-231 (231), MDA-MB-468 (468) or BT20 triple negative tumor cells or FIG. 13(F) against U937 or KG-1 myeloid leukemic cells; FIG. 13(G) illustrates cytokine concentration in supernatants that had been harvested from treated breast cancer co-cultures and FIG. 13(H) illustrates cytokine concentration in supernatants that had been harvested from treated leukemia co-cultures (n=2).

FIG. 16(A) shows the tumor burden as indicated by bioluminescence from malignant cells on data 4, 11, 19 and 26 after administration and FIG. 16(B) shows the weight of the mice over the period of the test. In each case, the cyatarbine was injected as a single dose 24 hours before infusion of γδ T-cells.

COMPARATIVE EXAMPLE A

In previous studies, the applicants have shown that healthy donors have 19,916±29,887 (mean±SD, n=21) circulating γδ T-cells. By comparison, patients with newly diagnosed EOC had 14,240±15,215 γδ cells/ml blood (mean±SD, n=13; not statistically significant (NS)) [16].

To enrich these cells, peripheral blood mononuclear cells (PBMC) were activated with ZA and cultured in AB serum-containing RPMI 1640 medium, supplemented with IL-2/IL-15. Specifically, PBMC isolated from normal (healthy) donors (n=21 separate donors) and from patients with EOC (n=13 separate donors) were cultured with ZA (1 µg/ml day 1 only), IL-2 (100 U/ml) and IL-15 (10 ng/ml). Cytokines and medium were added daily.

Figure 1:
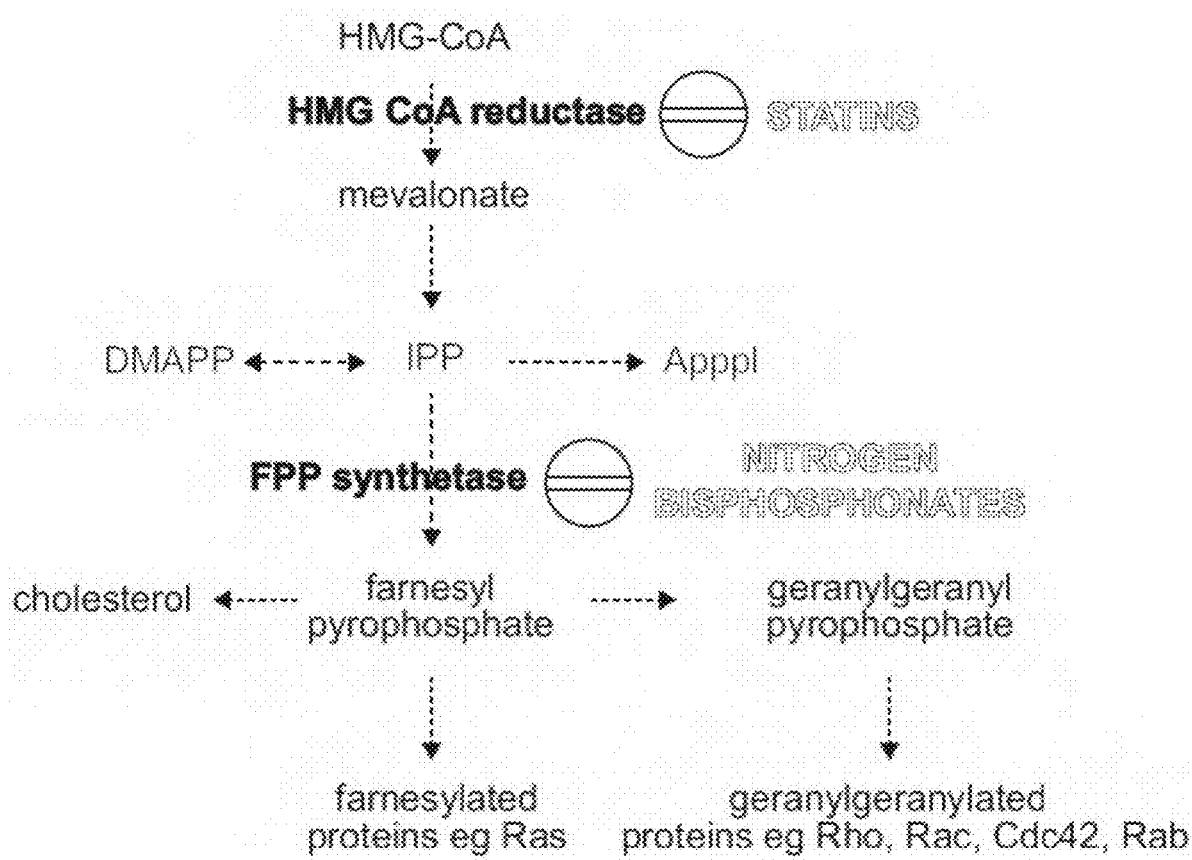
FIG. 1 is a schematic view showing the mevalonate pathway. Phosphoantigens (PAg) recognized by Vγ9Vδ2 T-cells include DMAPP, IPP and Apppl. Points of inhibition of the pathway by amino-bisphosphonates and statins are indicated by circles where IPP=Isopentenyl diphosphate and DMAPP=Dimethylallyl diphosphate.
Figure 2A:
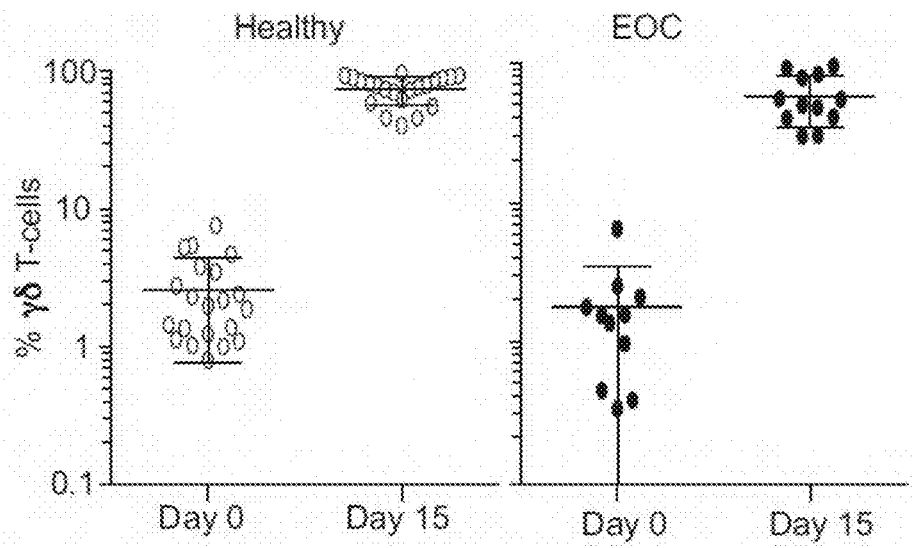
FIG. 2A shows the results of ex-vivo expansion of Vγ9Vδ2 T-cells using a comparative method (Method 1). After culture using conditions described above, the percentage of γδ T-cells per 20 ml blood sample was evaluated at initiation of the culture period and after 15 days.
Figure 2B:
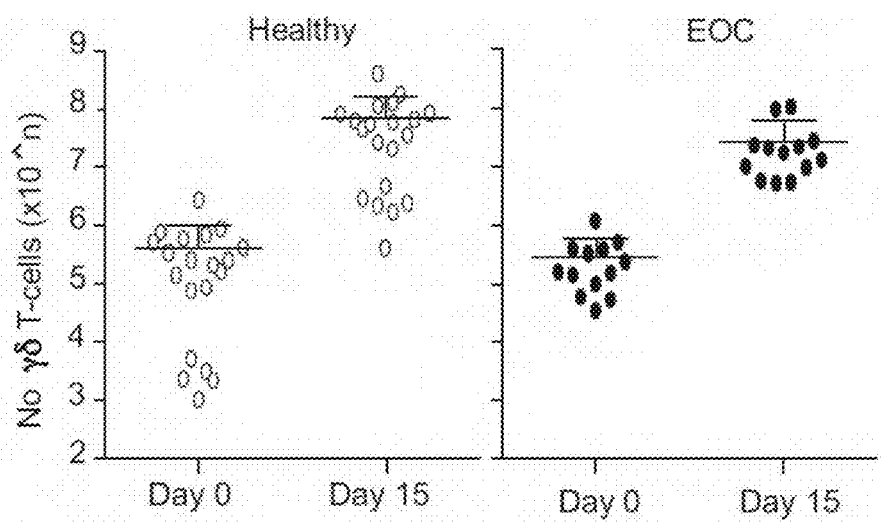
FIG. 2B shows the results of ex-vivo expansion of Vγ9Vδ2 T-cells using a comparative method (Method 1). After culture using conditions described above, the absolute number of γδ T-cells per 20 ml blood sample was evaluated at initiation of the culture period and after 15 days.

The percentage number of γδ T-cells and the absolute number of γδ T-cells per 20 ml blood sample was evaluated at initiation of the culture period and after 15 days. The results are shown in FIGS. 2(A) and 2(B) respectively. This "research grade" method resulted in an average expansion of γδ T-cells by 97-fold (EOC patients) or 172-fold (healthy donors; NS) (FIG. 2B).

Figure 2C:
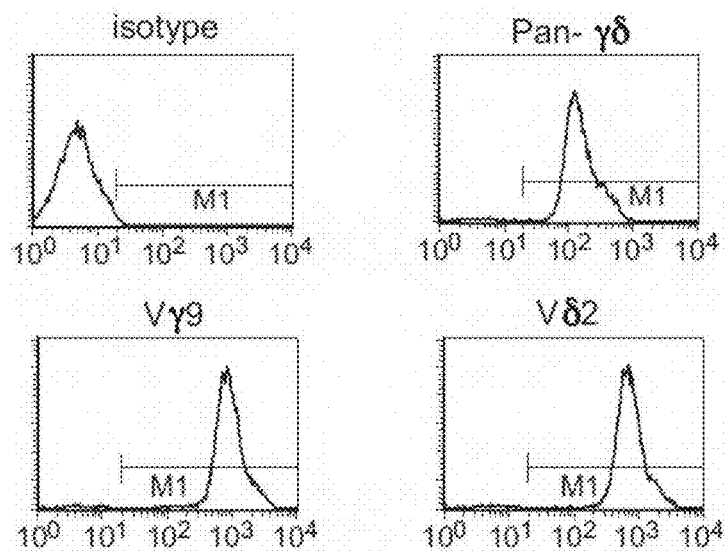
FIG. 2C presents expression of the expected Vγ9 and Vδ2 T-cell receptor subunits as determined by flow cytometry.

Expression of the expected Vγ9 and Vδ2 T-cell receptor subunits was determined by flow cytometry and the results are shown in FIG. 2(C). As is clear, eexpanded γδ T-cells from patients and healthy donors expressed the Vγ9Vδ2 T-cell receptor.

Figure 2D:
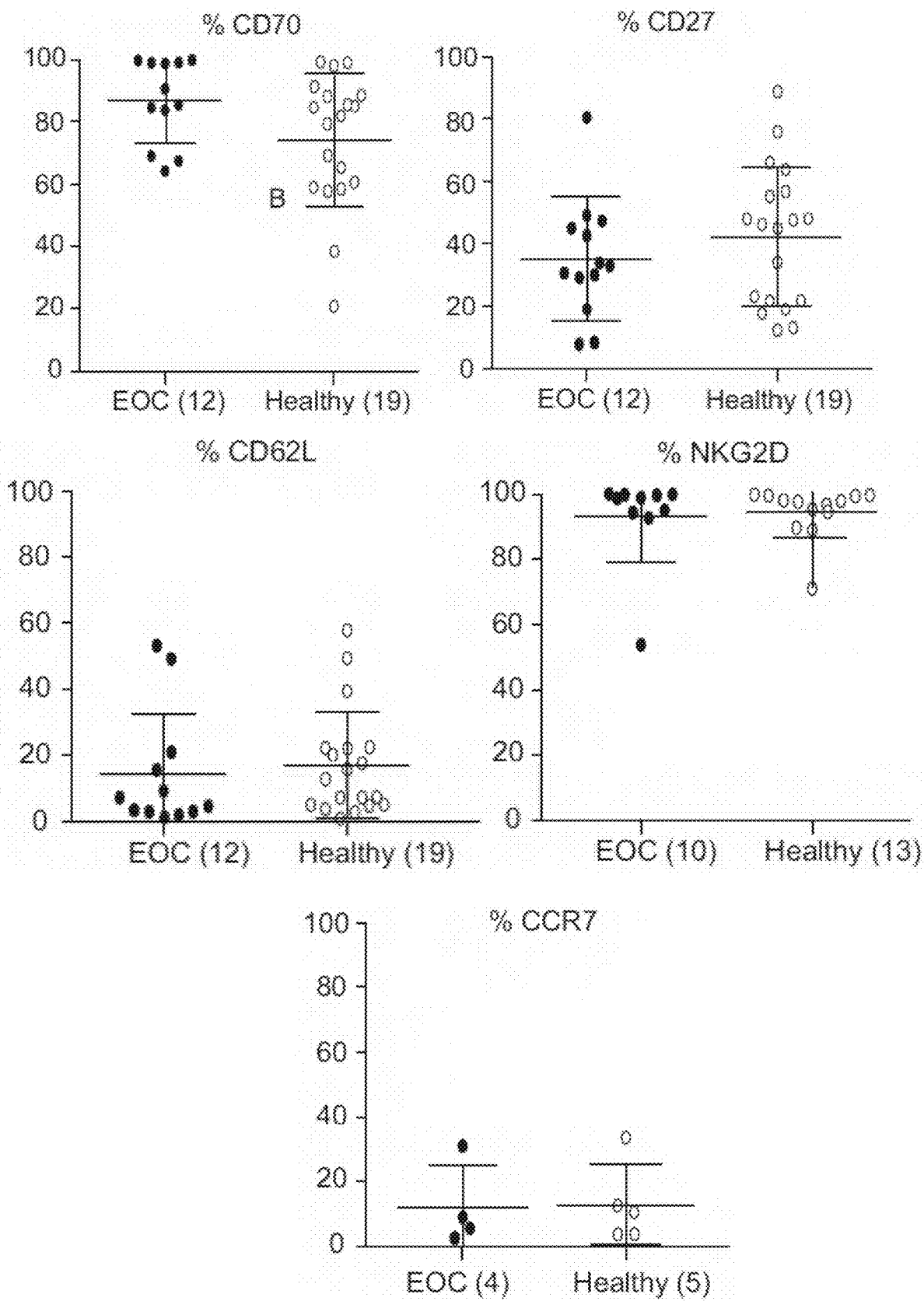
FIG. 2D shows pooled representative immunophenotypic data of γδ T-cells, expanded ex-vivo for 15 days from healthy donors and women with newly diagnosed EOC (donor number indicated in brackets).
Figure 2E:
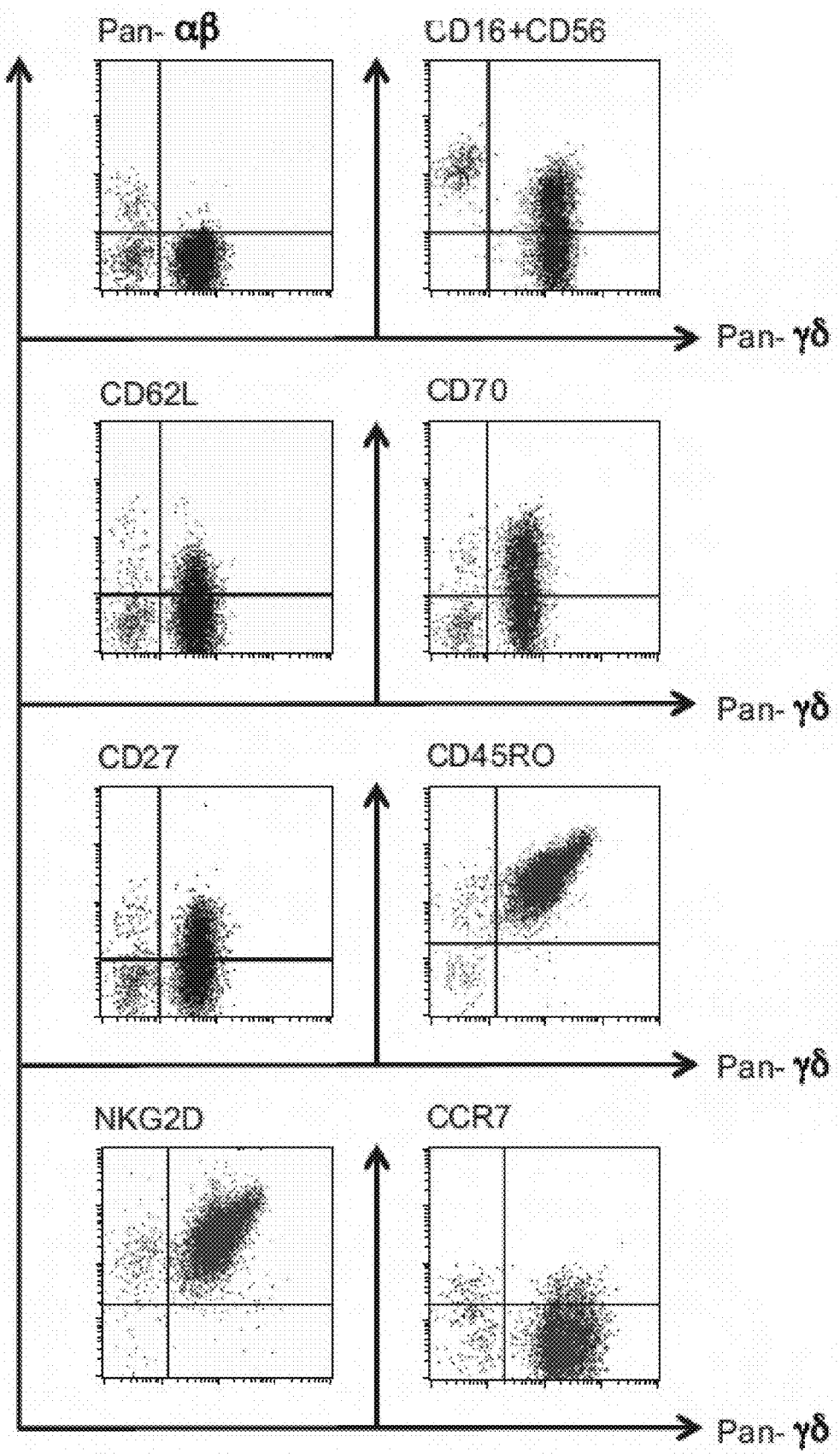
FIG. 2E shows representative immunophenotypic data of γδ T-cells, expanded ex-vivo for 15 days from healthy donors and women with newly diagnosed EOC (donor number indicated in brackets).

Pooled and representative immunophenotypic data of γδ T-cells, expanded ex-vivo for 15 days from healthy donors and women with newly diagnosed EOC (donor number indicated in brackets) was also obtained and the results are shown in FIGS. 2(D) and 2(E) respectively. There was a predominance of γδ T-cells, with small numbers of contaminating γδ T-cells and natural killer (CD16+56$^+$, CD3) cells. Expanded cells predominantly exhibit an effector and effector memory phenotype, which is similar in patients and healthy volunteers. We subsequently found that addition of IL-15 made no significant difference to the yield of cells obtained and this was omitted from subsequent expansion runs (data not shown).

Figure 3A:
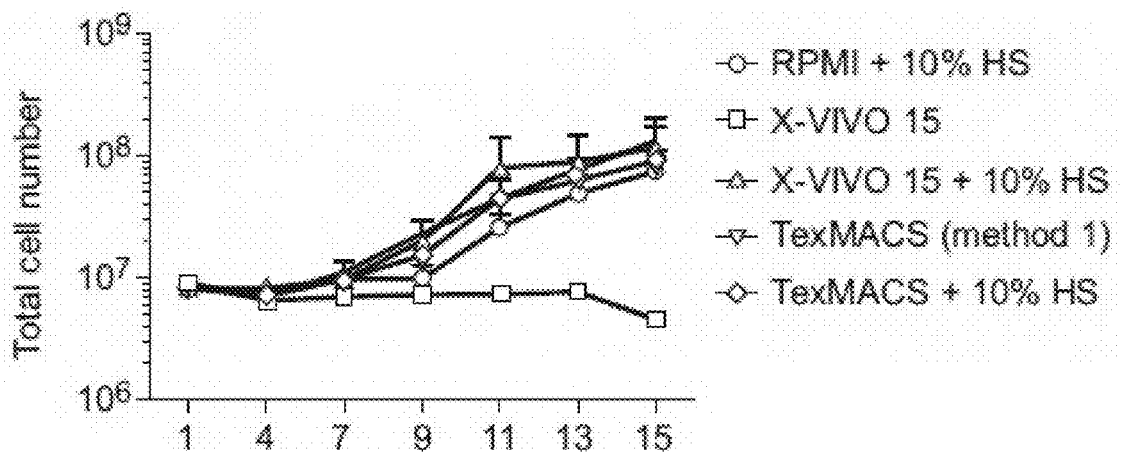
FIG. 3A shows the total cell number of γδ T-cells after expansion of Vγ9Vδ2 T-cells in various media, with and without human AB serum using comparative method 1 after 14 days of culture.
Figure 3B:
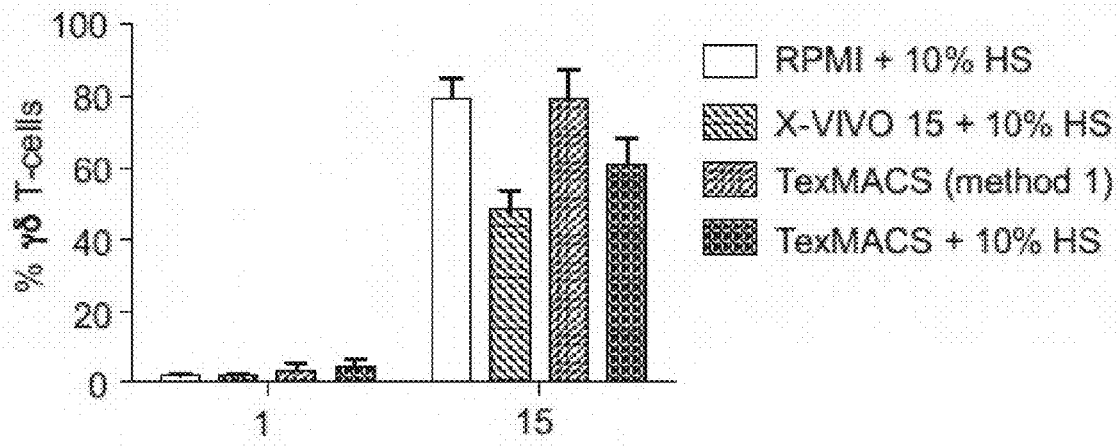
FIG. 3B shows the % γδ T-cells present after expansion of Vγ9Vδ2 T-cells in various media, with and without human AB serum using comparative method 1 after 14 days of culture.
Figure 3C:
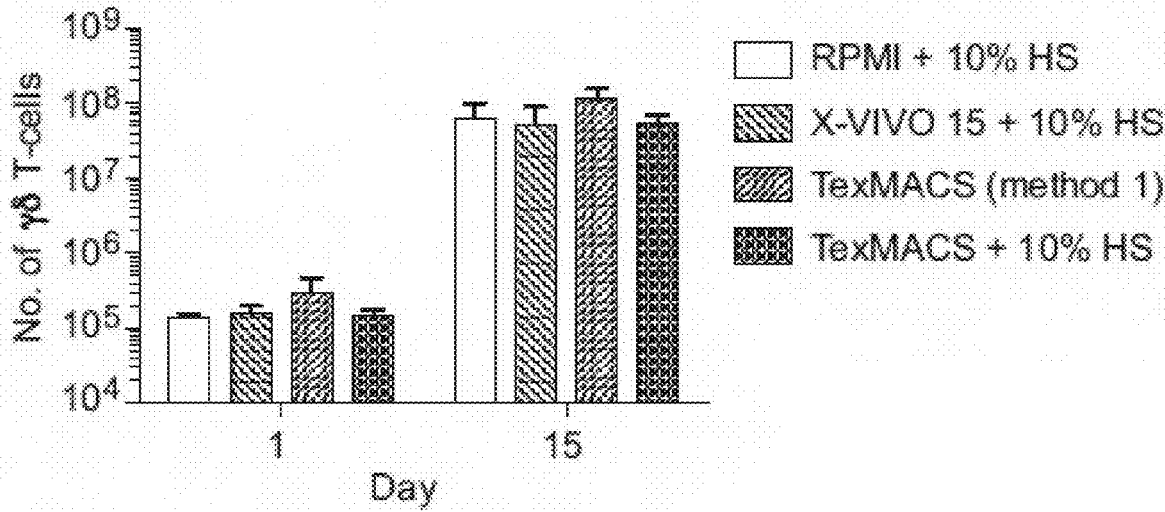
FIG. 3C shows the yield of γδ T-cells after expansion of Vγ9Vδ2 T-cells in various media, with and without human AB serum using comparative method 1 after 14 days of culture.

To adapt manufacture of γδ T-cell products for clinical use, we tested commercially available GMP media for their ability to support the expansion of these cells using ZA+IL-2. The method as described above was repeated using clinical grade serum-free medium. PBMC were cultured in RPMI+10% human AB serum or two commercially available GMP grade media, with or without 10% human AB serum. In each case, ZA (1 µg/ml) was added to activate γδ T-cells, which were then expanded by addition of IL-2 (100 U/ml). The results are shown in FIGS. 3A-C. These show that the TexMACS medium in particular enables the expansion of these cells under serum-free conditions in "method 1".

Figure 4A:
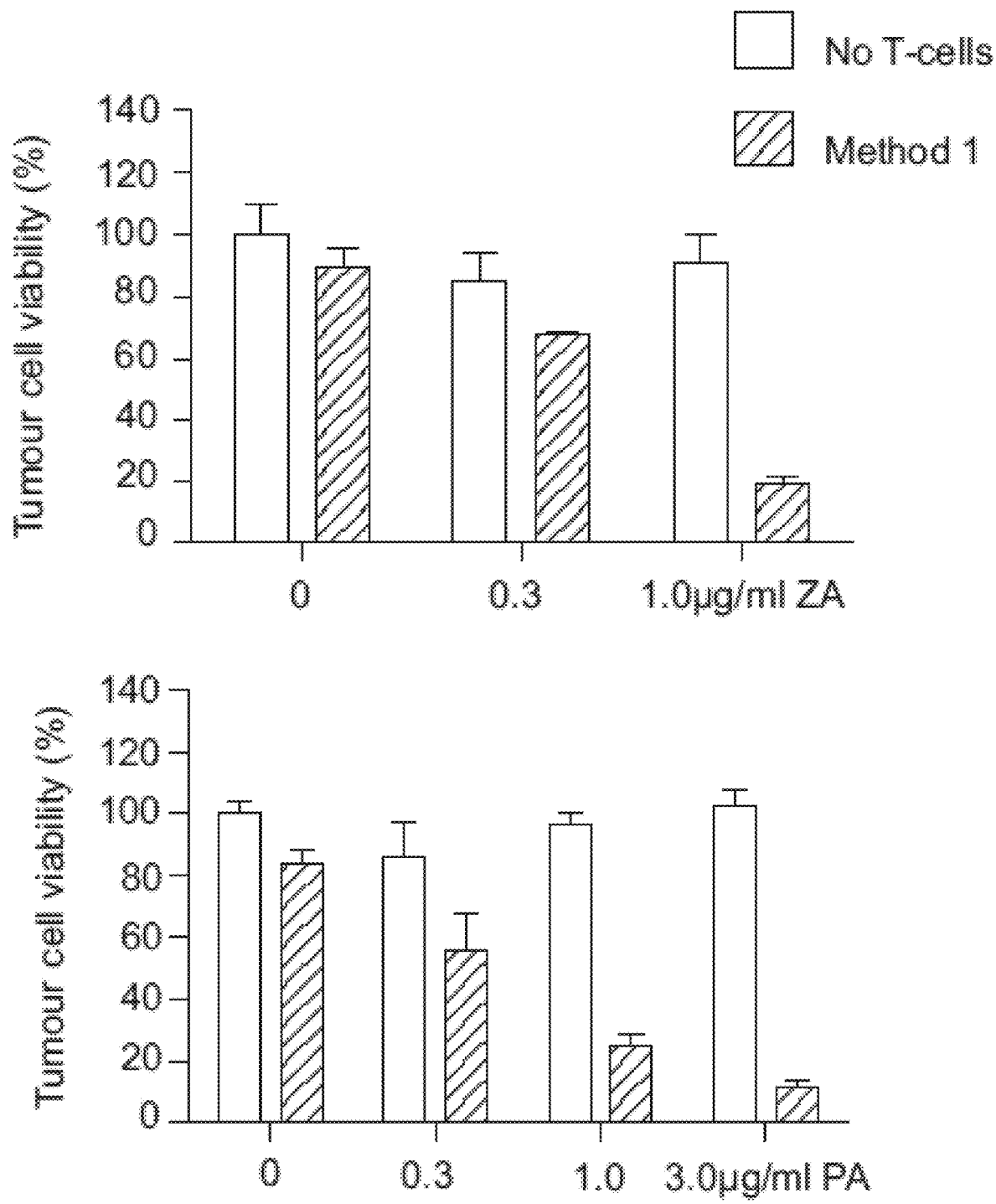
FIGS. 4A-F show the results of cytotoxicity assays using cells expanded using the comparative method 1 in an assay against a range of ovarian cancer cell lines as follows.
Figure 4B:
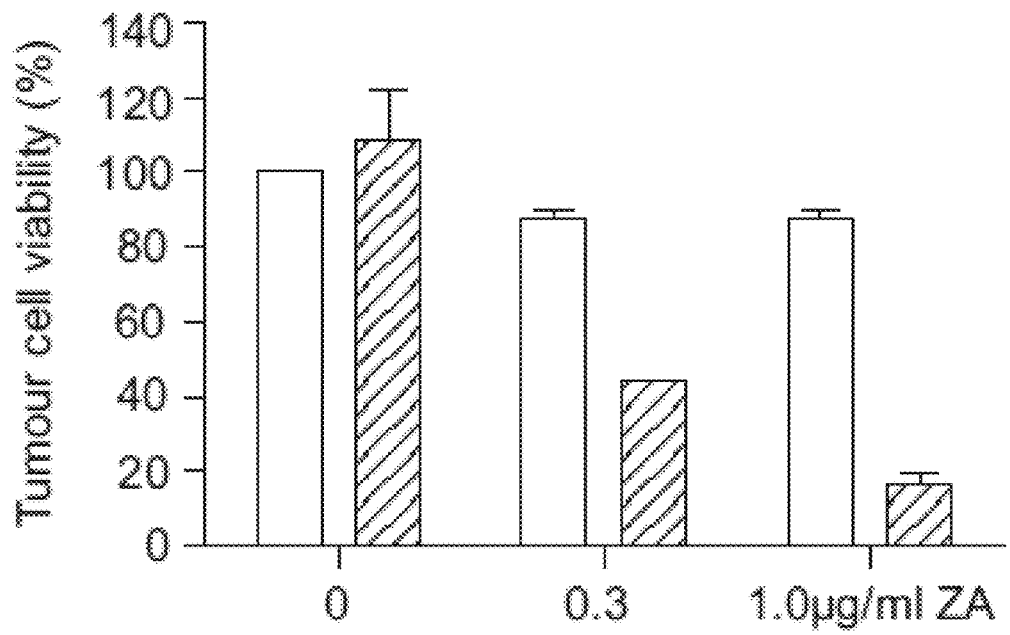
Figure 4B:
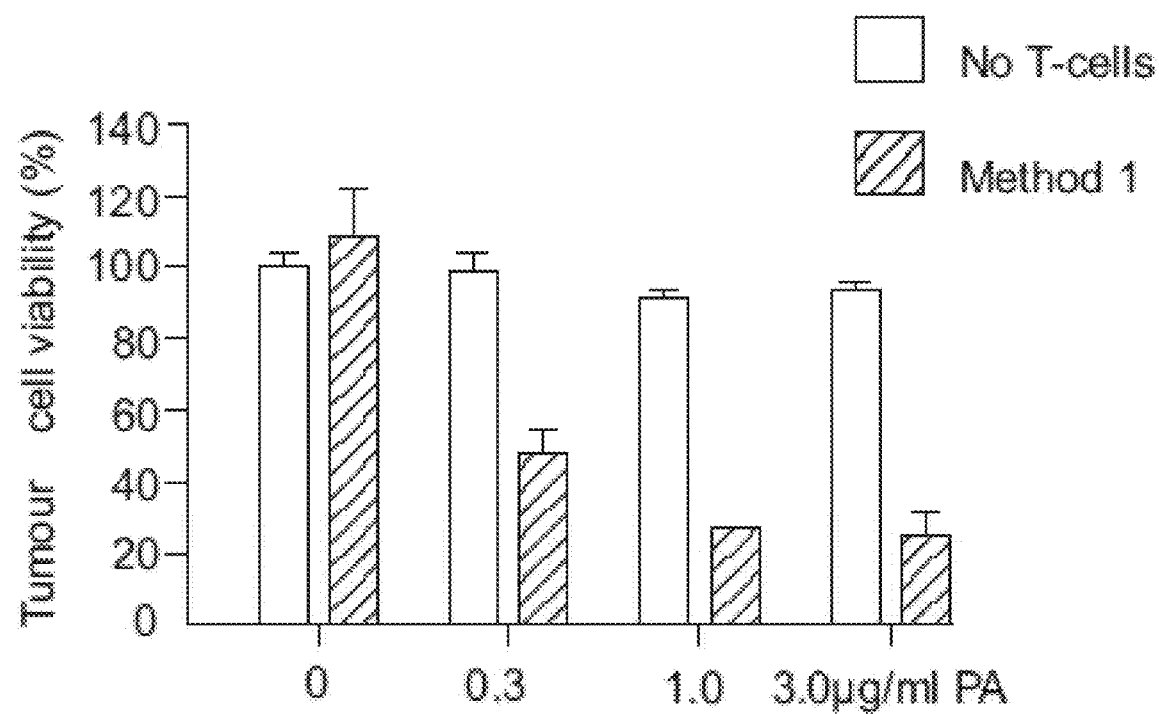
Figure 4C:
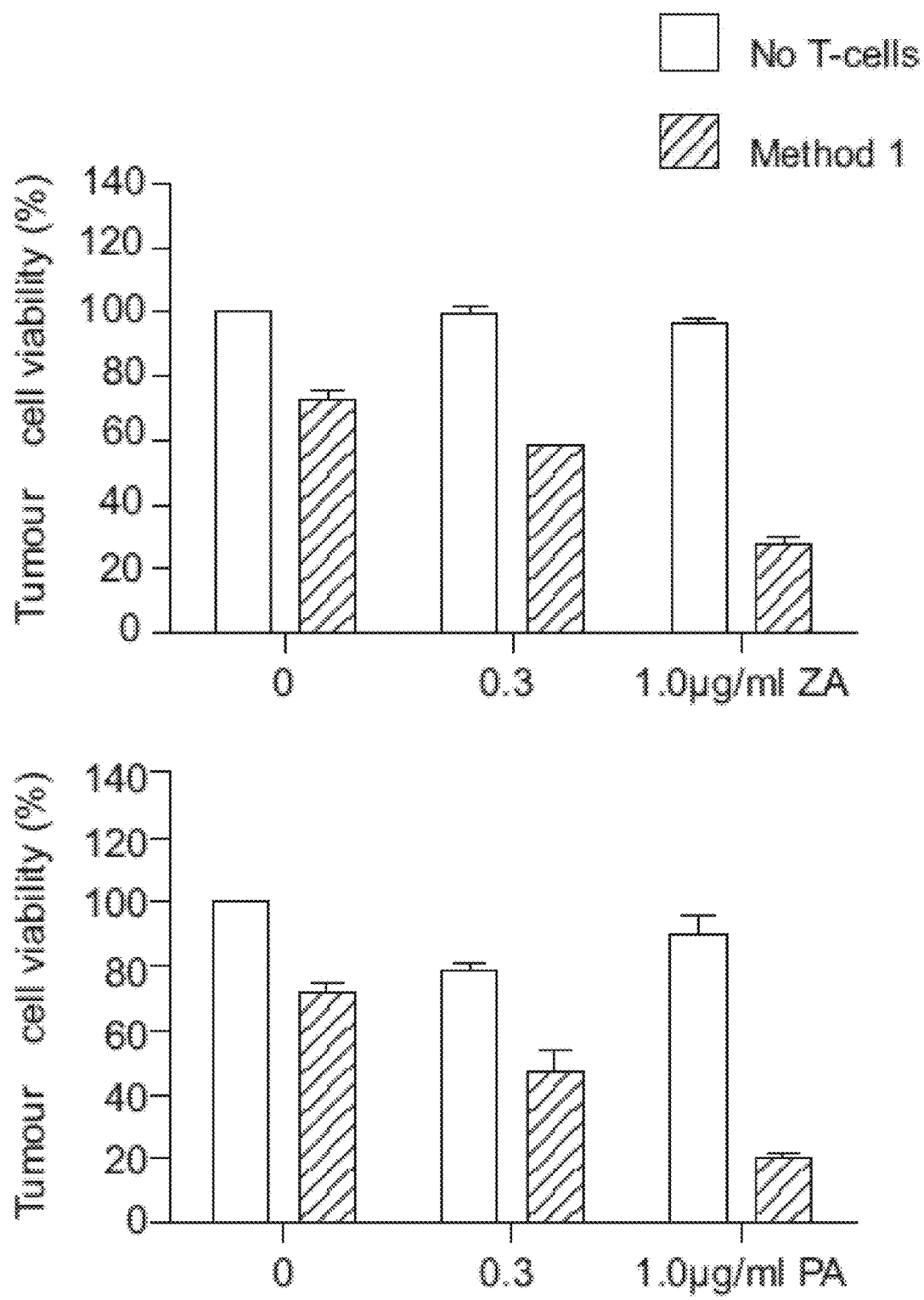
Figure 4D:
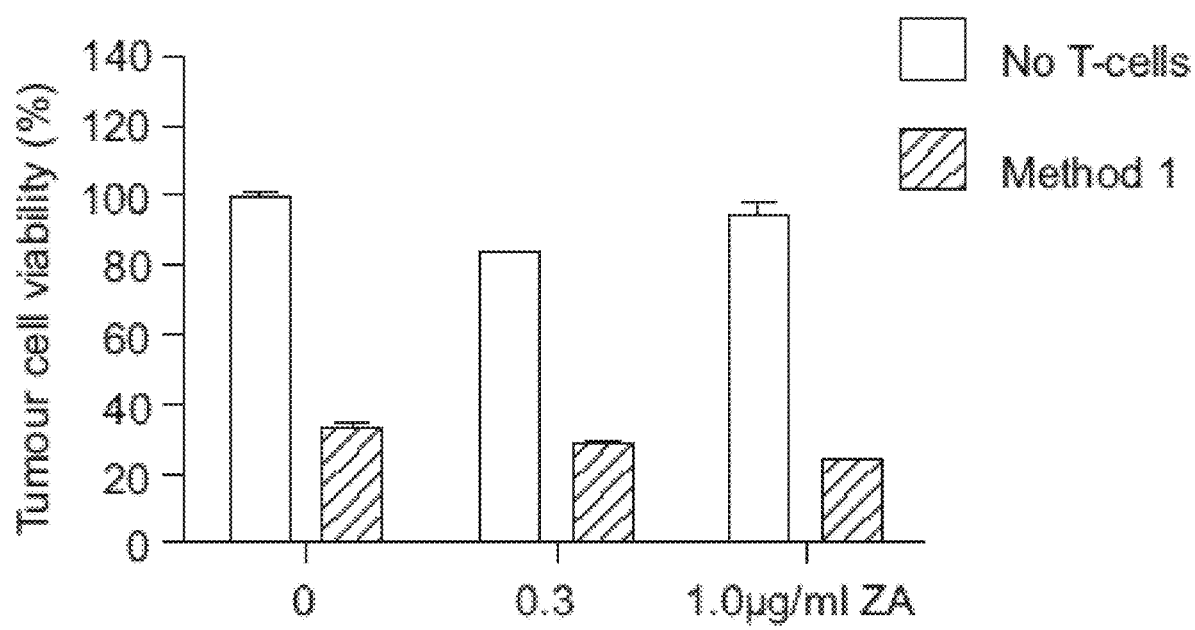
Figure 4D:
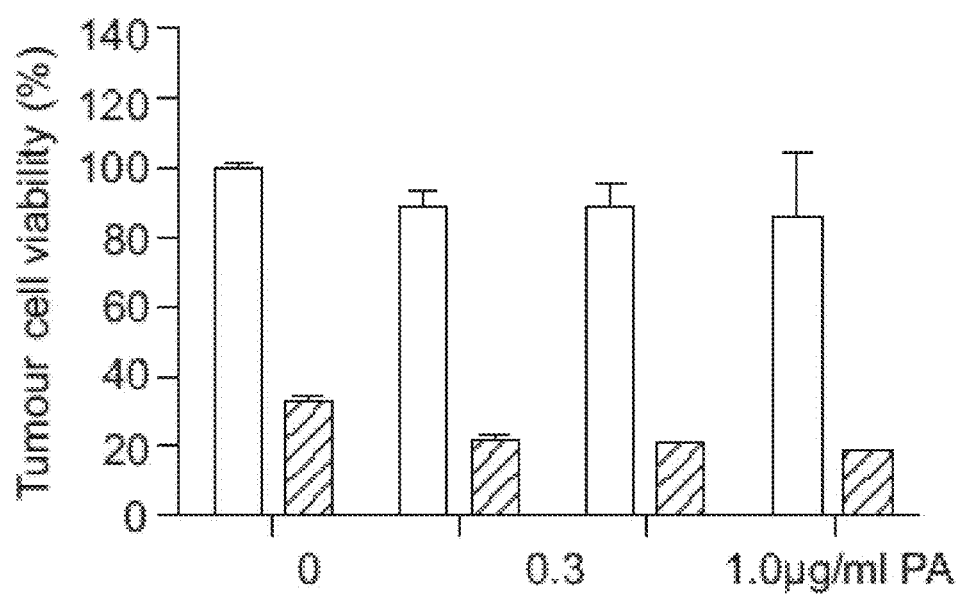
Figure 4E:
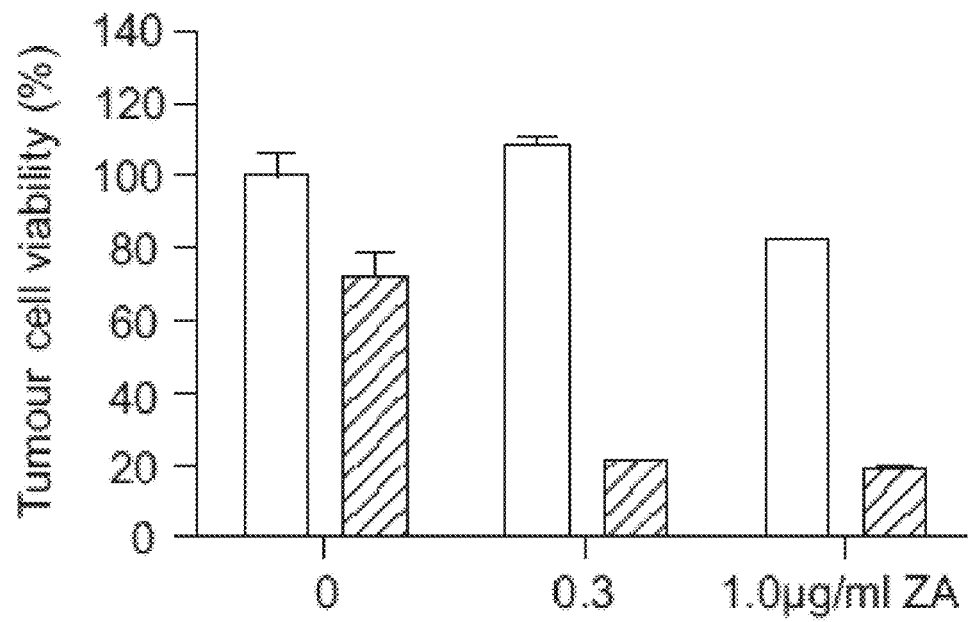
Figure 4E:
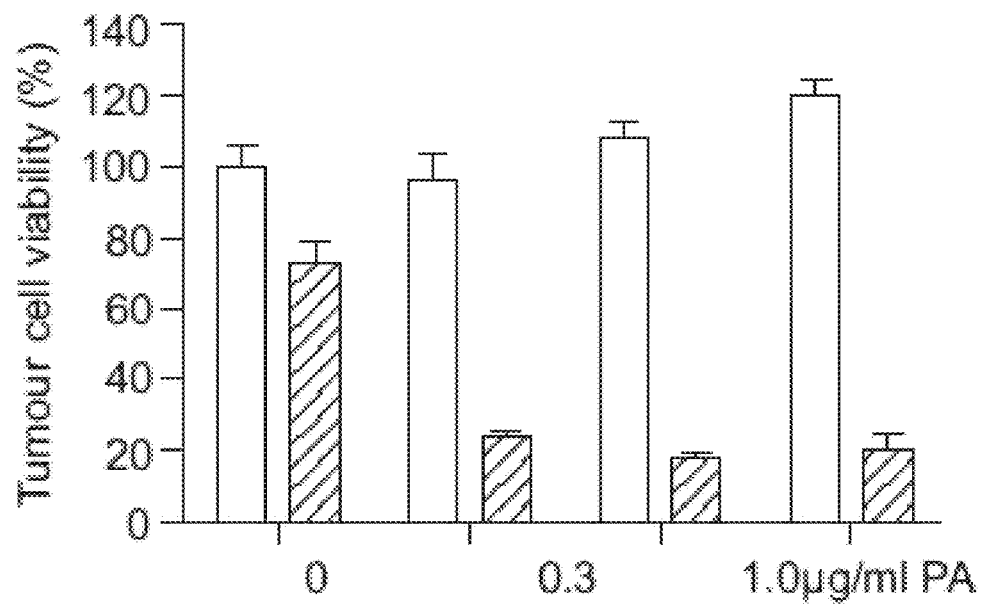
Figure 4F:
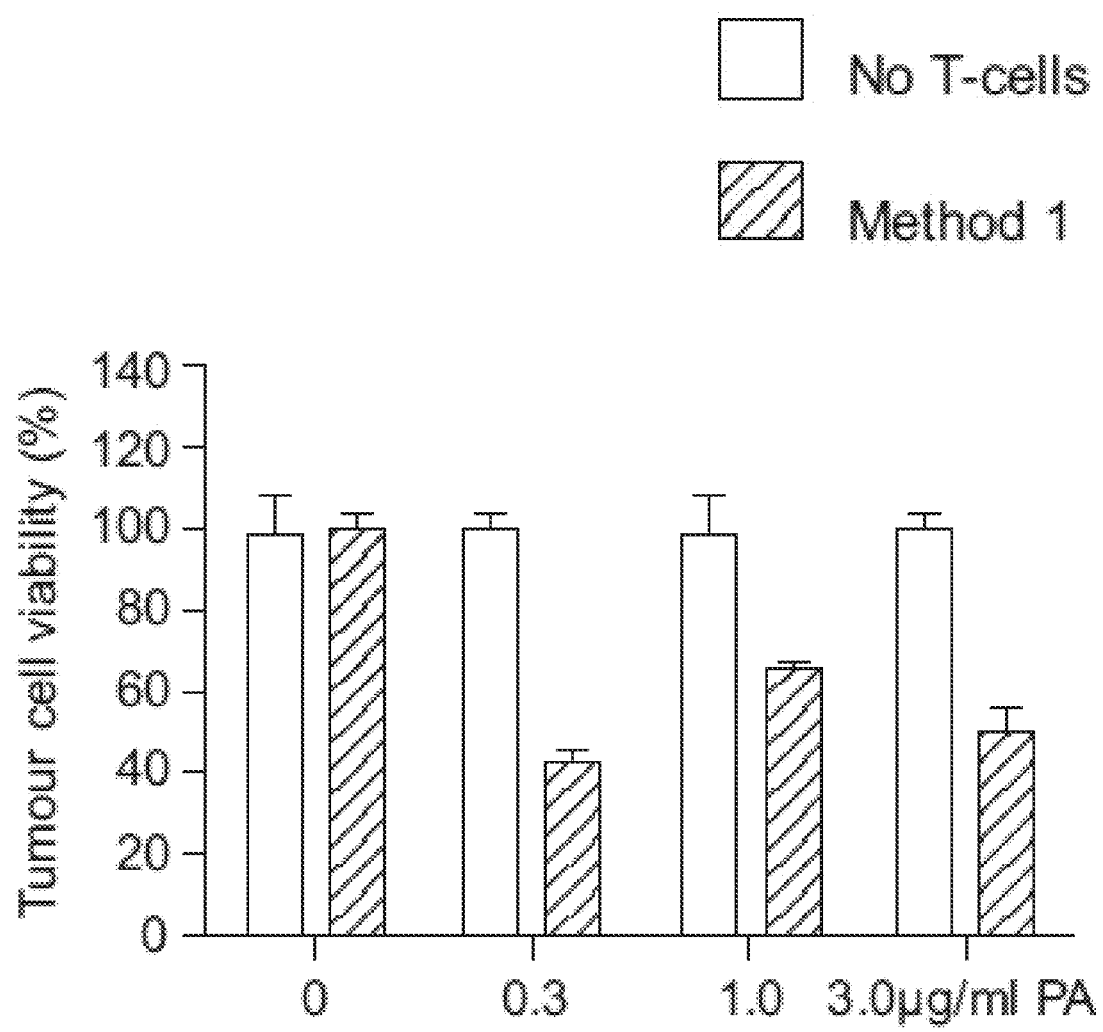

Cytotoxicity assays were established in triplicate at a 5:1 effector:target ratio in 96 well plates and the results are shown in FIGS. 4A-F. Where indicated, tumor cells were pulsed for 24 h with the indicated concentration of zoledronic (ZA) or pamidronic acid (PA), prior to addition of γδ T-cells. Residual tumor cell viability was measured after overnight co-culture with Vγ9Vδ2 T-cells by MTT assay for FIG. 4(A) IGROV-1; FIG. 4(B) KOC7C; FIG. 4(C) PEO1; FIG. 4(D) PEA; FIG. 4(E) SKOV-3; FIG. 4(F) TOV-21G. The results show that Vγ9Vδ2 T-cells expanded using method 1 exhibited broad and NBP-enhanced anti-tumor activity against a range of ovarian and other tumor cell lines.

EXAMPLE 1

Expansion of T-Cells in Accordance with the Invention.

Next, we modified method 1 such that transforming growth factor (TGF)-β was added together with IL-2 at all times. This approach is referred to hereafter as method 2.

In a variation of the method of Example A above, blood was collected from healthy donors or patients, in a tube with citrate anticoagulant. Using Ficoll-Paque (GE), PBMCs were isolated according to previously published methodology [17].

Isolated PBMC cells were then reconstituted in GMP TexMACS Media (Miltenyi) at $3 \times 10^6$ cell/mL. To the reconstituted cells, 1 µg/mL Zoledronic Acid (Zometa, Novartis) was added as an activator, together with 100 U/mL IL-2 and 5 ng/mL TGF-β. The cells were incubated at 37° C. in air containing 5% carbon dioxide.

On day 3, cells were fed with 100 U/mL IL-2 and 5 ng/mL TGF-β. Thereafter, on days 4, 7, 9, 11, 13, 15, cells were counted by trypan exclusion using a hemocytometer. If the number of T-cells was less than $1 \times 10^6$ cells/mL, a further 100 U/mL IL-2 and 5 ng/mL TGF-β were added. If the number of T-cells was between $1 \times 10^6$ and $2 \times 10^6$ cells/mL, an equivalent volume of TexMACS medium was added together with 100 U/mL IL-2 and 5 ng/mL TGF-β. If the number of T-cells was greater than 2×10⁶ cells/nL, double the volume of TexMACS media was added together with 100 U/mL IL-2 and 5 ng/mL TGF-β.

Figure 5A:
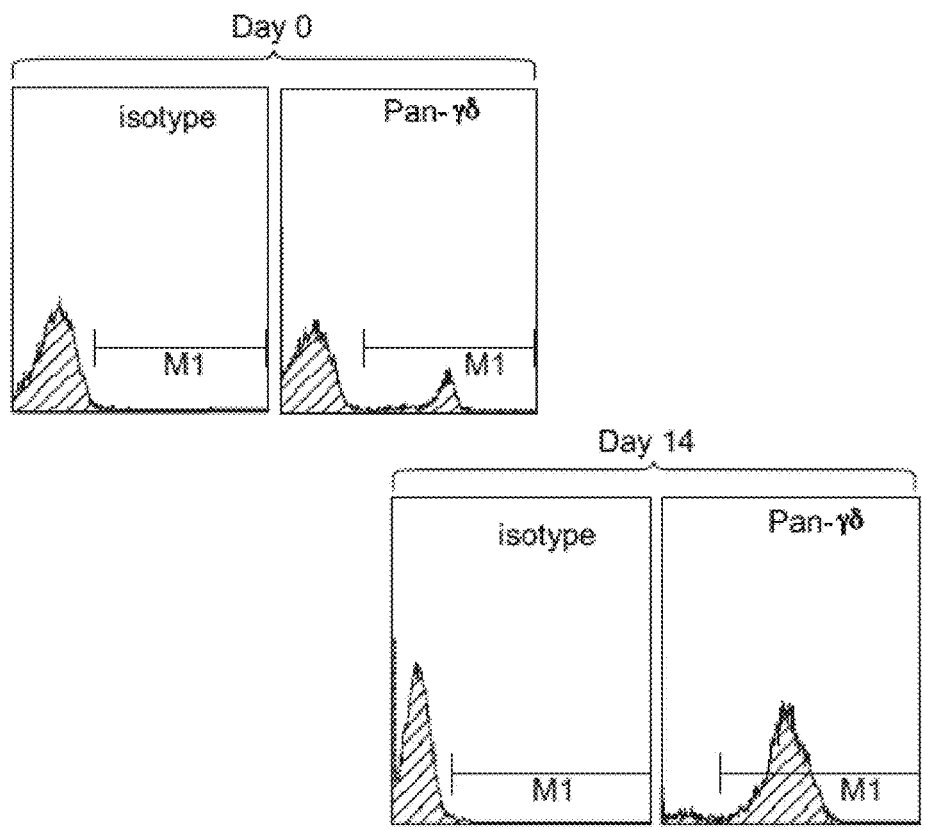
FIGS. 5A-B show the results obtained using a method to expand Vγ9Vδ2 T-cells ex-vivo in accordance with the invention.
Figure 5B:
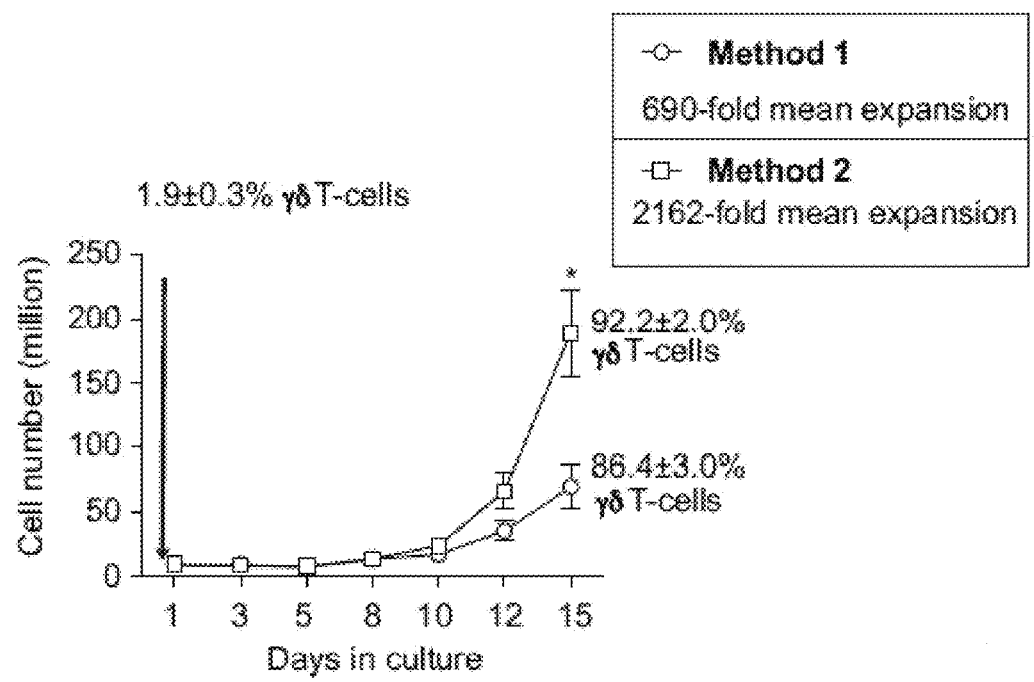

After 15 days, the cells were analyzed by flow cytometry with a pan γδ antibody to confirm the enrichment of γδ T-cells in these cultures. The results are shown in FIGS. 5A-B. These show that the modified method achieves enrichment FIG. 5(A) and improved expansion FIG. 5(B) of Vγ9Vδ2 T-cells (mean±SEM, n=13 independent replicates).

Figure 6A:
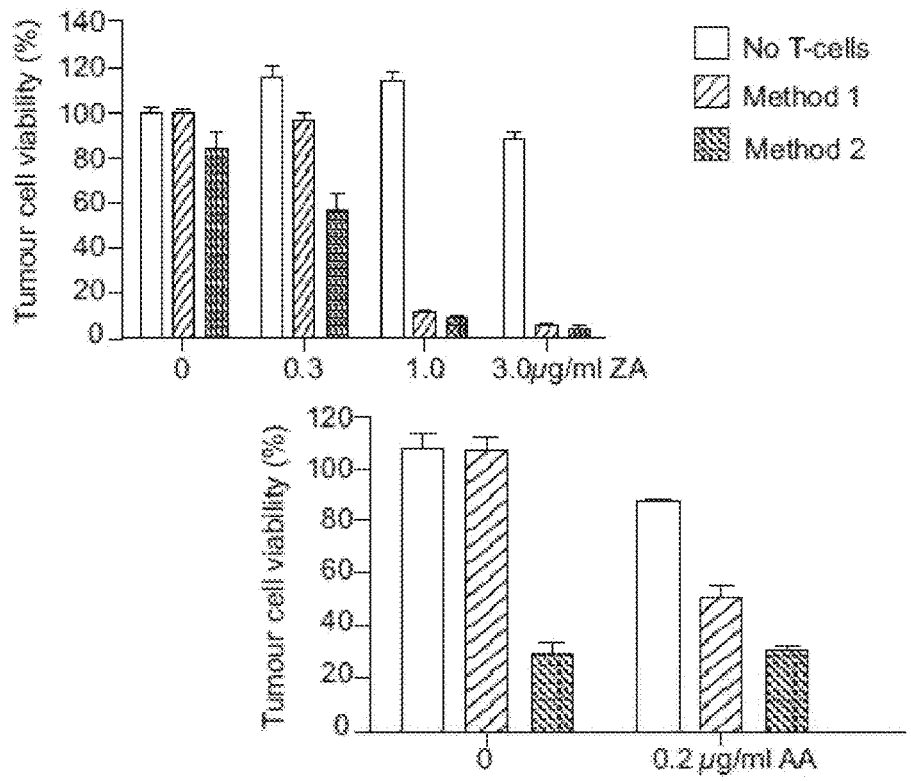
FIGS. 6A-I show the comparative anti-tumor activity of method 1 and method 2-expanded γδ T-cells. After expansion of γδ T-cells for weeks using either method 1 or 2, cytotoxicity assays were established in triplicate at a 5:1 effector:target ratio in 96 well plates. Tumor cells were cultured with the indicated aminobisphosphonates for 24 hours prior to undertaking the cytotoxicity assay. After overnight co-culture with Vγ9Vδ2 T-cells, residual tumor cell viability was measured by MTT or luciferase assay. Data show mean±SEM tumor cell killing from 2-5 independent replicate experiments performed using the indicated ovarian cancer cell lines FIG. 6(A) IGROV-1, FIG. 6(B) SKOV-3, FIG. 6(C) Kuramochi and FIG. 6(D) TOV-21G; myeloid leukemic cell lines FIG. 6(E) U937 and FIG. 6(F) KG-1 and breast cancer cell lines FIG. 6(G) MDA-MB-231, FIG. 6(H) MDA-MB-468 and FIG. 6(I) BT-20.
Figure 6B:
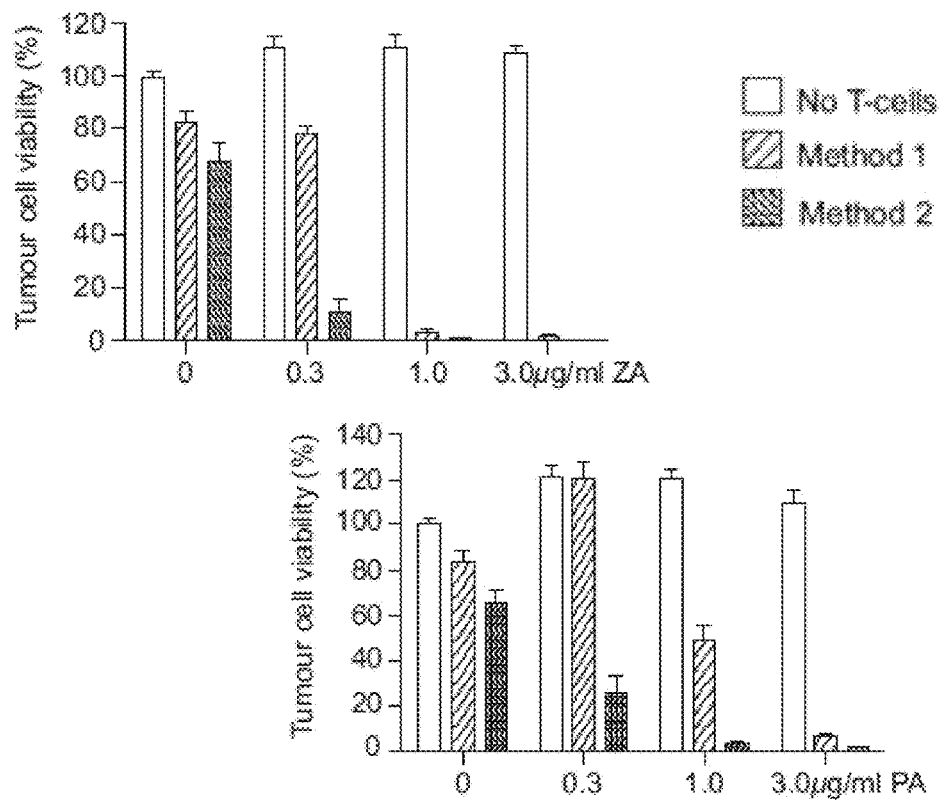
Figure 6C:
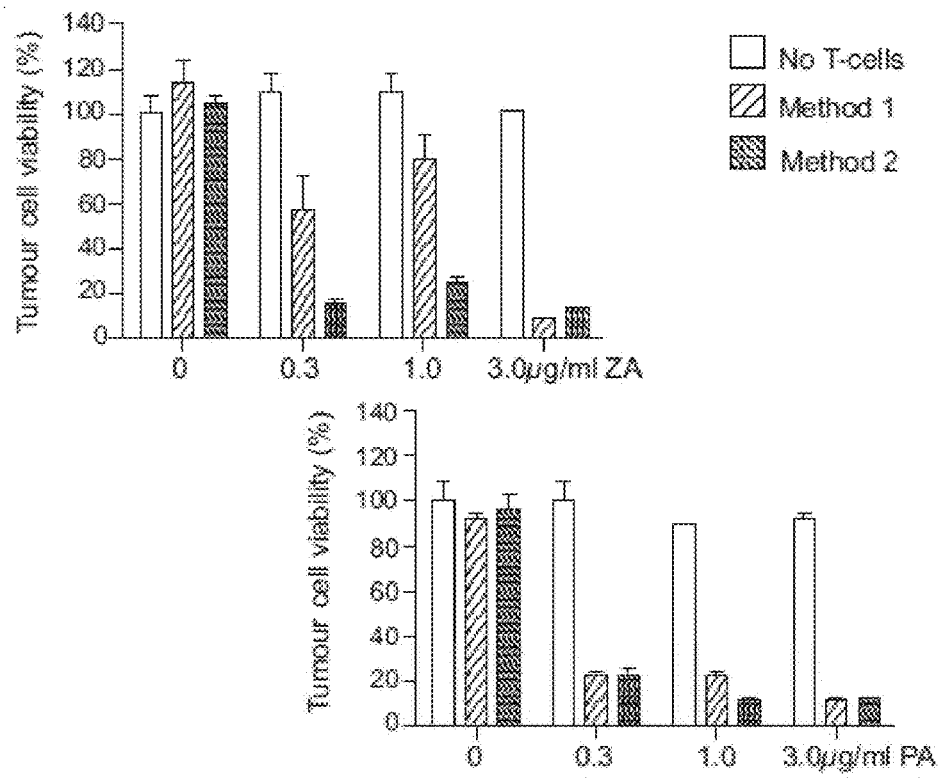
Figure 6D:
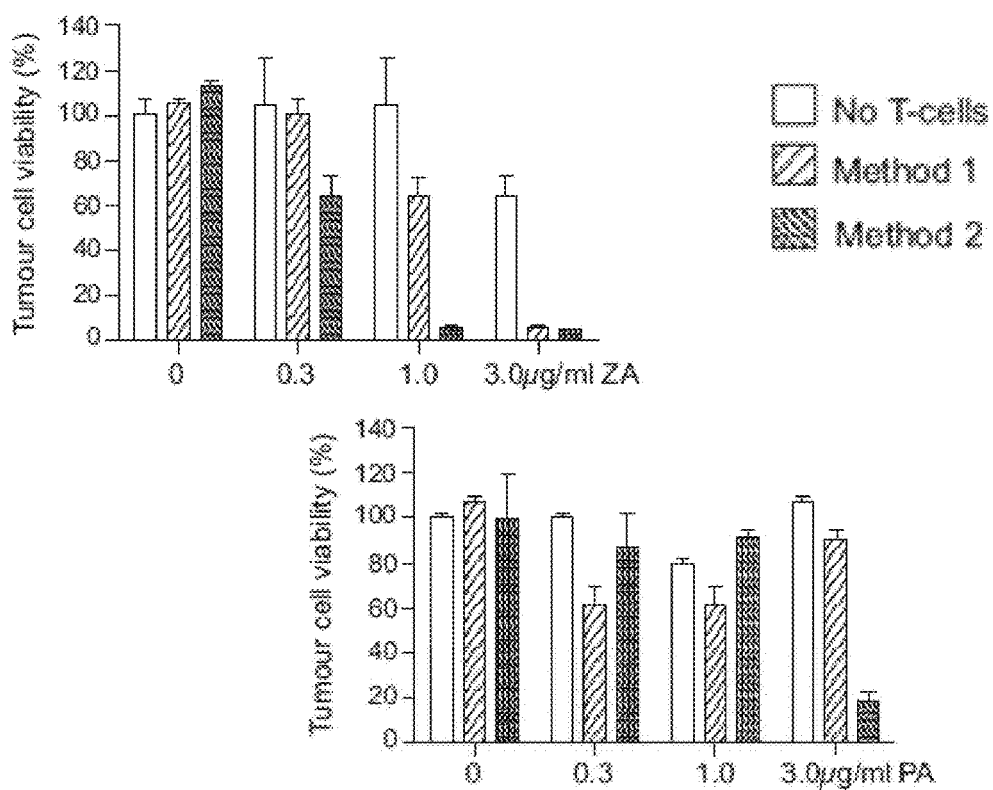
Figure 6E:
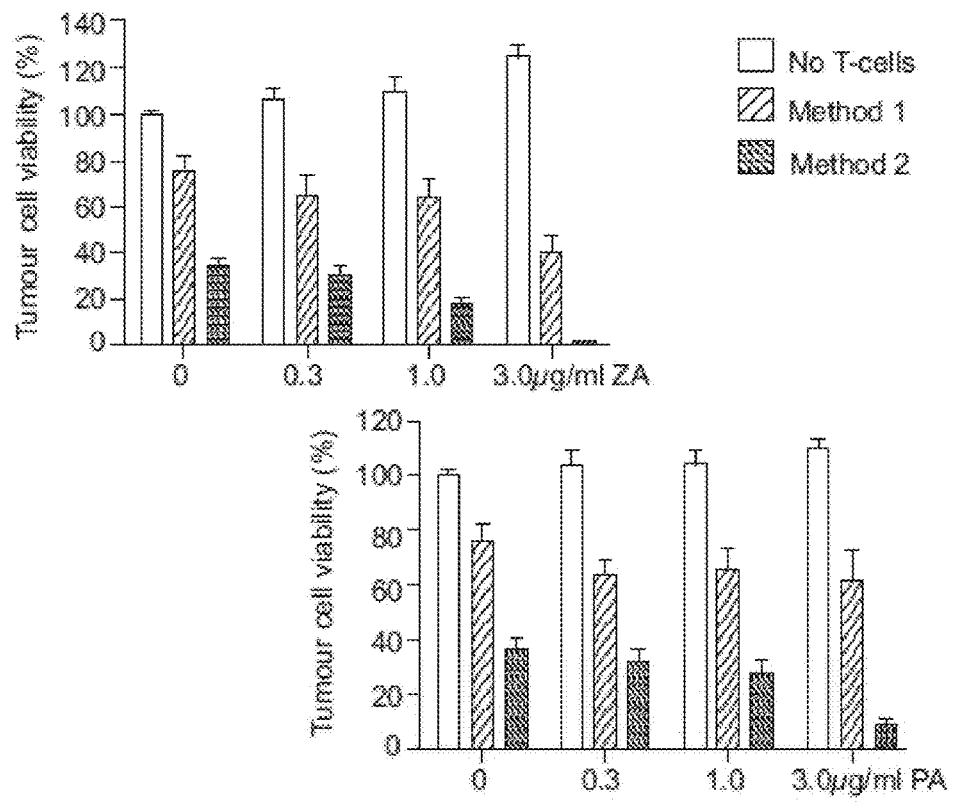
Figure 6F:
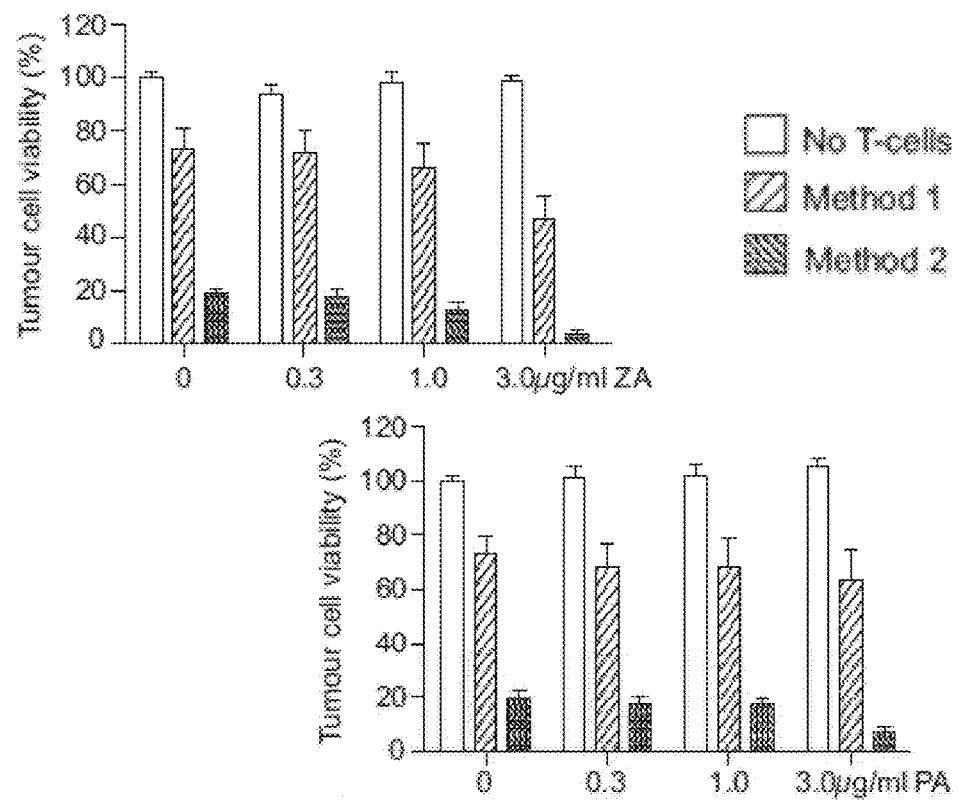
Figure 6G:
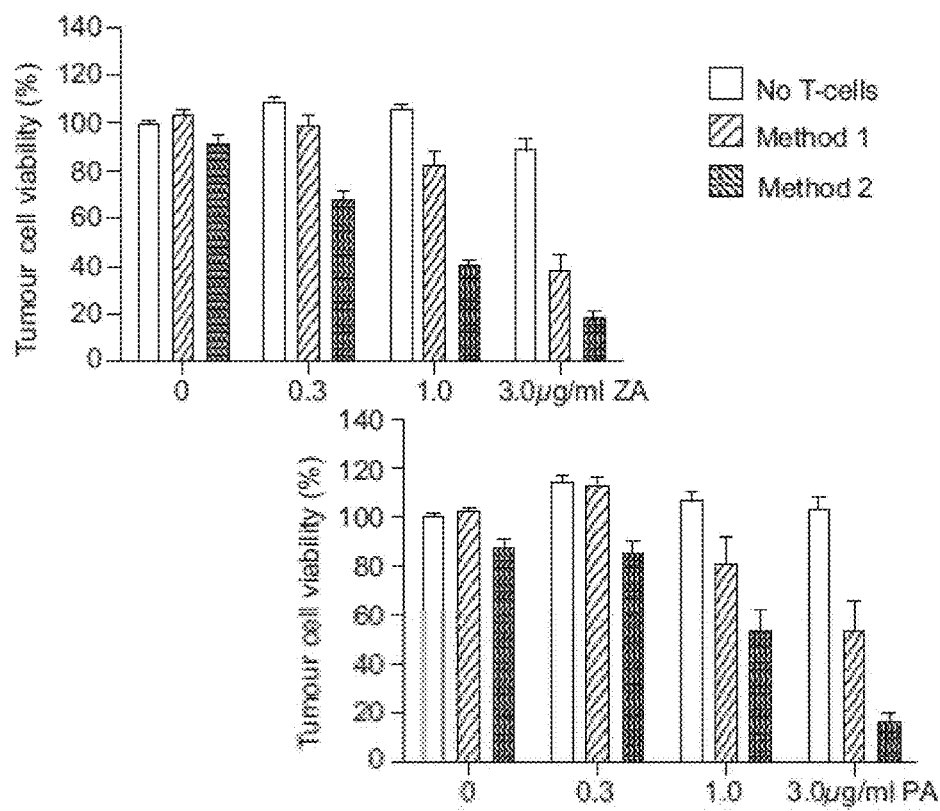
Figure 6H:
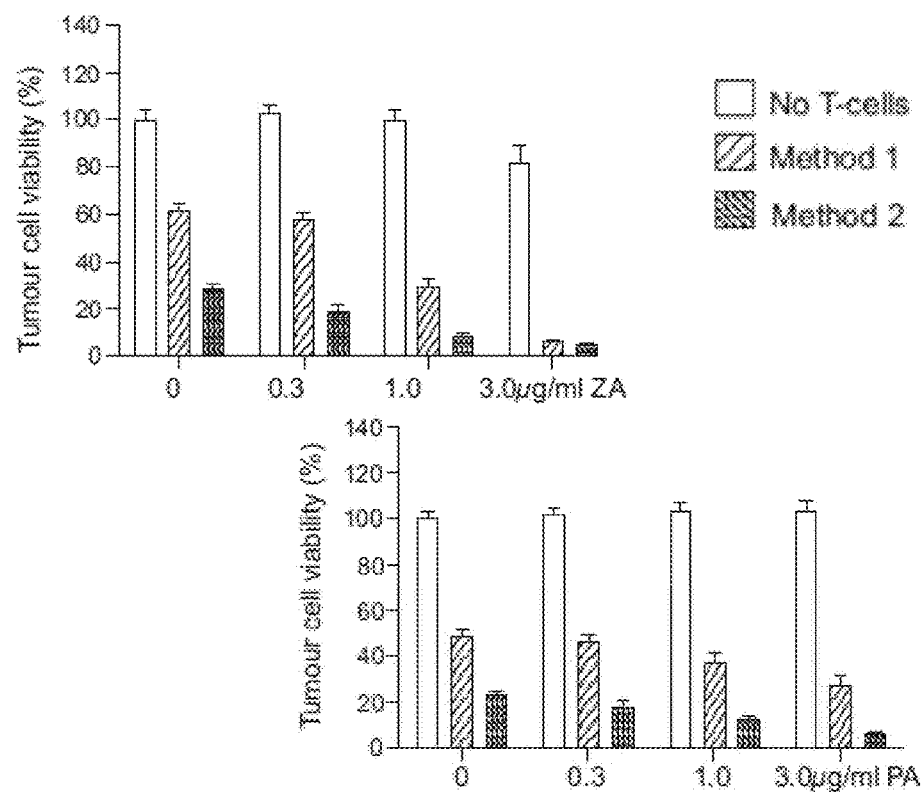
Figure 6I:
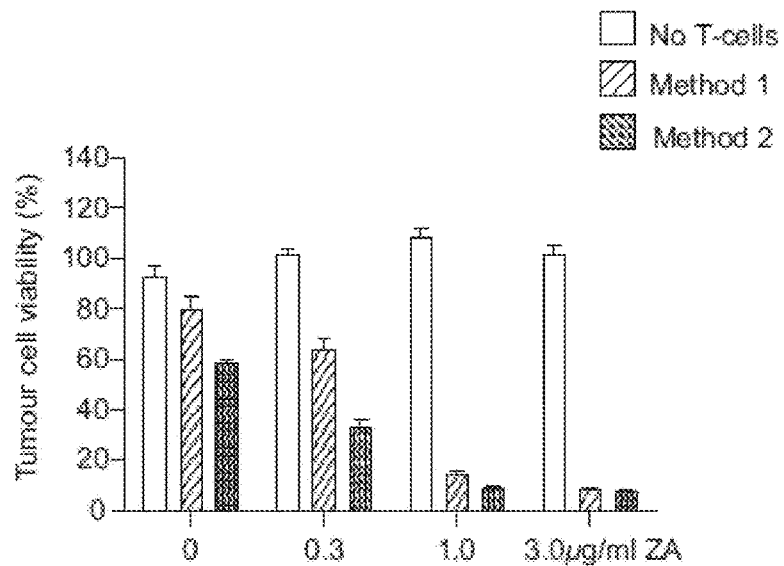
Figure 6I:
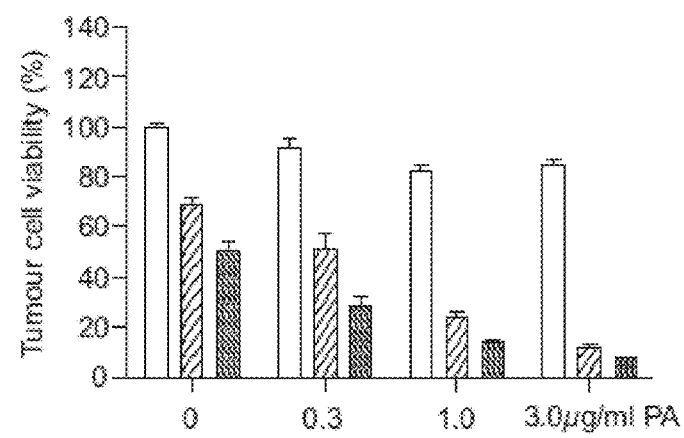

Additionally, the T-cells were immunophenotypically characterised and subjected to functional tests. The relative ability of the T-cells obtained using method 1 above, or the present method of the invention to mediate cytotoxic destruction of tumor cells was evaluated. After expansion of γδ T-cells for 2 weeks using either method 1 or 2, cytotoxicity assays were established in triplicate at a 5:1 effector: target ratio in 96 well plates. Where indicated, tumor cells were pulsed for 24 h with the indicated concentration of zoledronic (ZA), alendronic acid (AA) or pamidronic acid (PA), prior to addition of γδ T-cells. Residual tumor cell viability was measured after overnight co-culture with Vγ9Vδ2 T-cells by MTT or luciferase assay. The results are shown in FIGS. 6A-I. FIG. 6(A) IGROV-1, FIG. 6(B) SKOV-3, FIG. 6(C) Kuramochi and FIG. 6(D) TOV-21G; myeloid leukemic cell lines FIG. 6(E) U937 and FIG. 6(F) KG-1 and breast cancer cell lines: FIG. 6(G) MDA-MB-231, FIG. 6(H) MDA-MB-468 and FIG. 6(I) BT-20.

Activation of γδ T-cells when co-cultivated with tumor cells was assessed by measurement of release of IL-2 and IFN-γ. Ability of these expanded γδ T-cells to control an established burden of malignant disease was also assessed in SCID Beige mice with an established burden of U937 myeloid leukemia.

The original rationale for inclusion of TGF-β in the culture process was to try to improve expression of homing receptors such as CXCR4 on these cells. Completely unexpectedly however, addition of TGF-β resulted in substantially enhanced yields of Vγ9Vδ2 T-cells as shown in FIGS. 5A-B.

Figure 10:
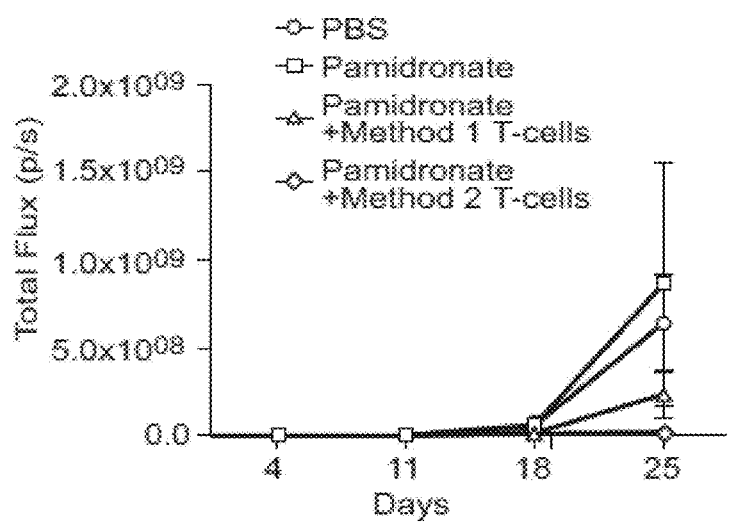
FIG. 10 shows the in-vivo therapeutic activity of intravenously administered expanded Vγ9Vδ2 T-cells obtained using method 1 and the method of the invention, against an established burden of malignant disease (U937 leukemia) in SCID Beige mice.

Method 2-expanded cell products also demonstrated equivalent or enhanced anti-tumor activity against EOC (IGROV-1, SKOV-3, Kuramochi, TOV-21G), breast cancer (MDA-MB-231) and myeloid leukemic cells (U937), even in the absence of NBP exposure (FIGS. 6A-I; FIG. 10). However, anti-tumor activity was consistently enhanced by prior NBP sensitization (FIGS. 6A-I).

Figure 7A:
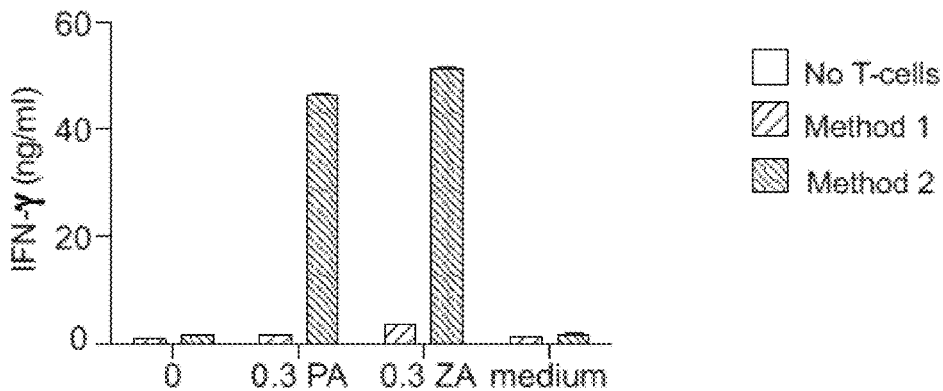
FIGS. 7A-O illustrate cytokine production by method 1 and method 2-expanded γδ T-cells. γδ T-cells were expanded using method 1 or 2 and then co-cultivated with bisphosphonate-pulsed or unpulsed tumor cells as described in FIG. 6. Supernatants were then harvested after 24 h of co-culture and analysed for interferon-γ FIGS. 7(A-I) and interleukin-2 FIGS. 7(J-O) by ELISA. Interferon (IFN)-γ production is shown for the following ovarian cancer cell lines FIG. 7(A) Kuramochi, FIG. 7(B) IGROV-1, FIG. 7(C) SKOV-3, FIG. 7(D) TOV-21G; breast cancer cell lines FIG. 7(E) MDA-MB-468.
Figure 7B:
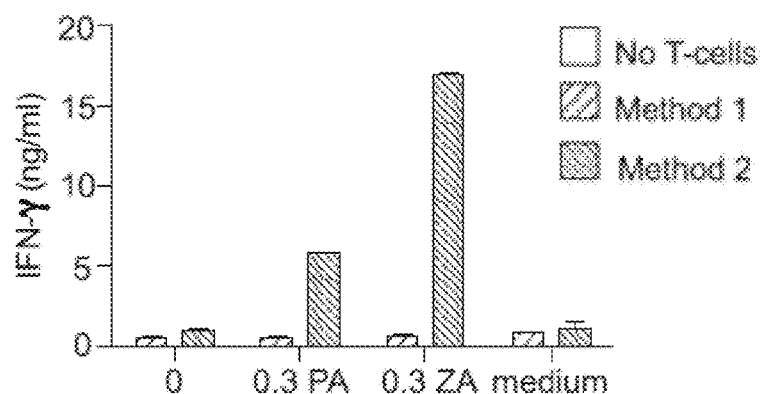
FIG. 7(F) MDA-MB-231.
FIG. 7(G) BT-20; myeloid leukemic cell lines FIG. 7(H) U937, FIG. 7(I) KG-1. Interleukin-2 production is shown for co-cultivation experiments undertaken with FIG. 7(J) Kuramochi, FIG. 7(K) U937, FIG. 7(L) KG-1, FIG. 7(M) MDA-MB-231, FIG. 7(N) MDA-MB-468 and FIG. 7(O) BT-20 tumor cells. Data show mean±SEM from 3-5 independent replicate experiments.
Figure 7C:
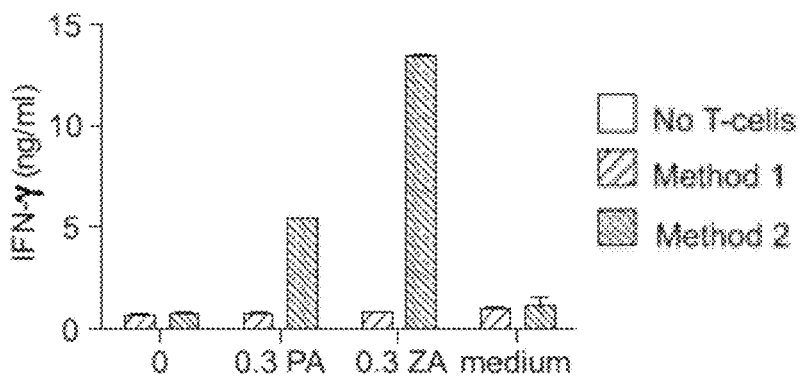
Figure 7D:
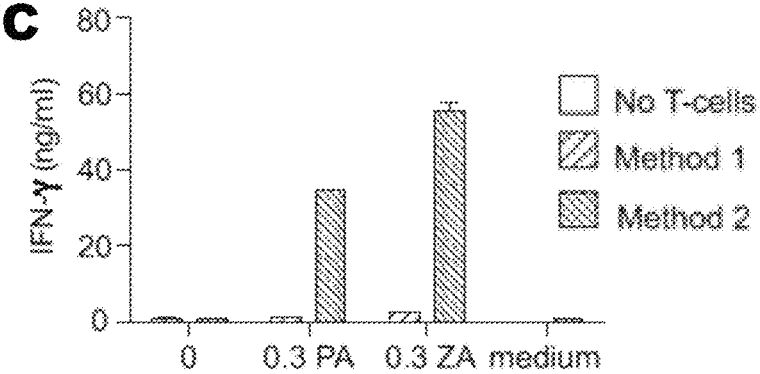
Figure 7E:
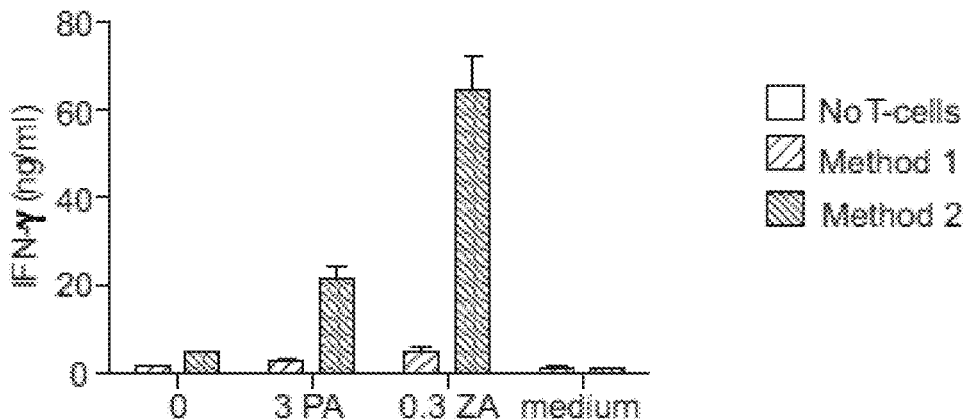
Figure 7F:
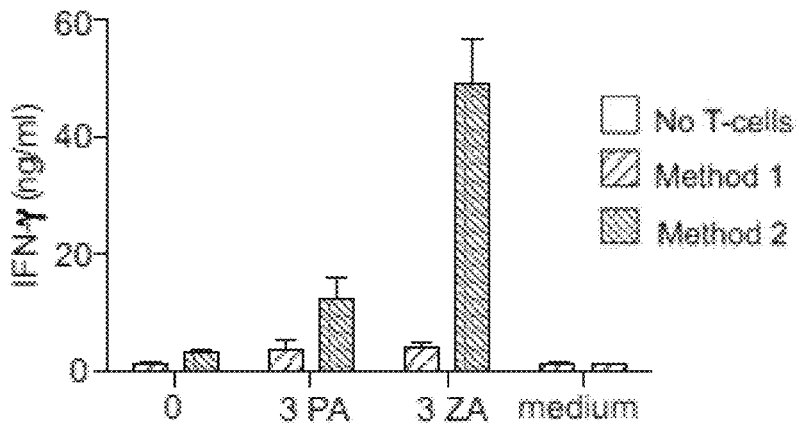
Figure 7G:
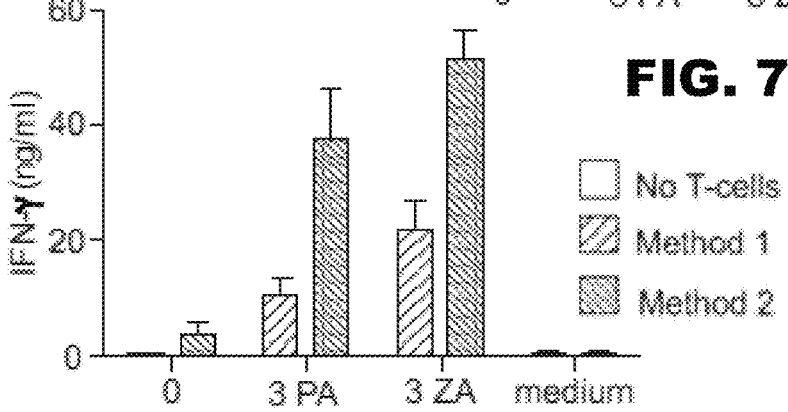
Figure 7H:
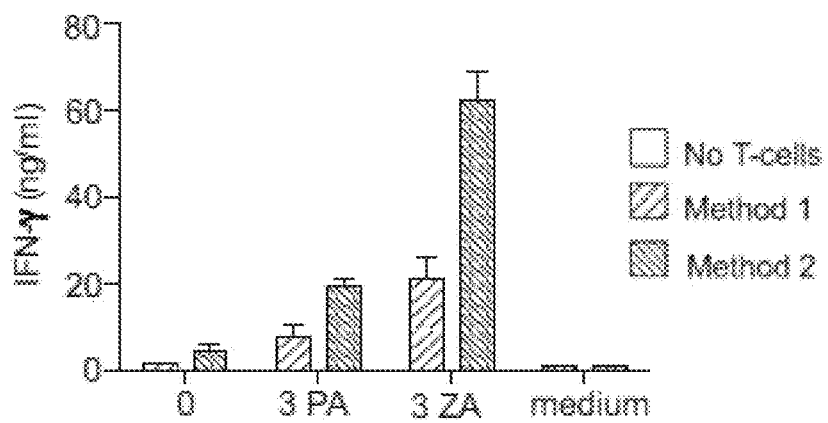
Figure 7I:
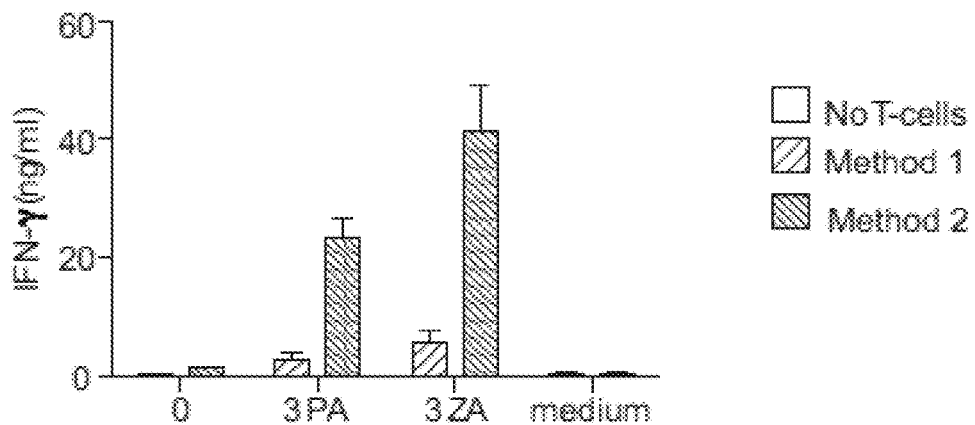
Figure 7J:
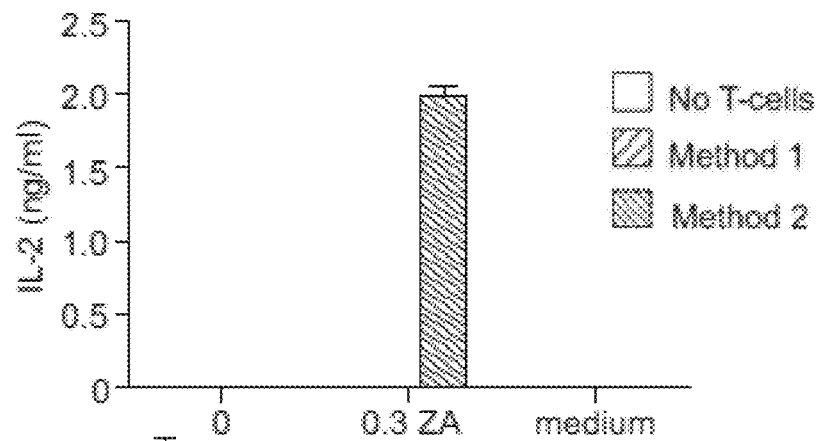
Figure 7K:
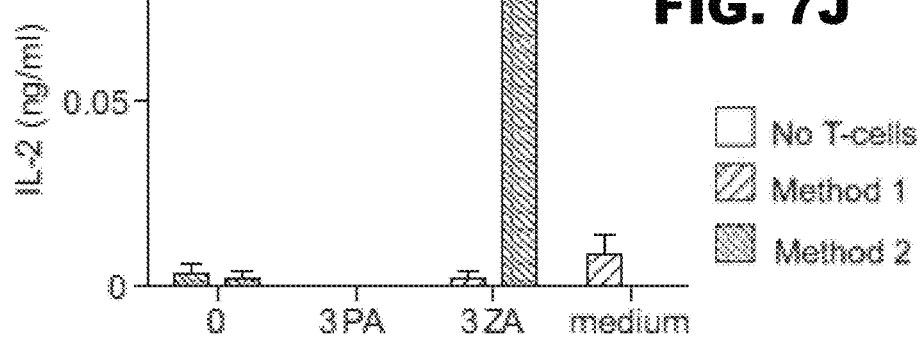
Figure 7L:
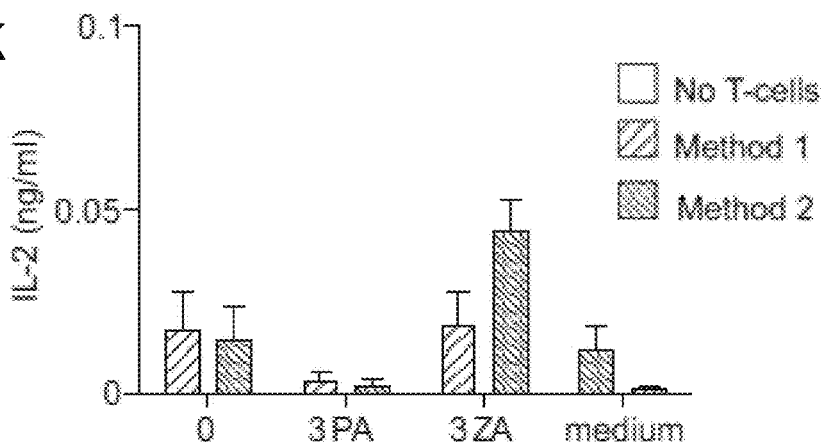
Figure 7M:
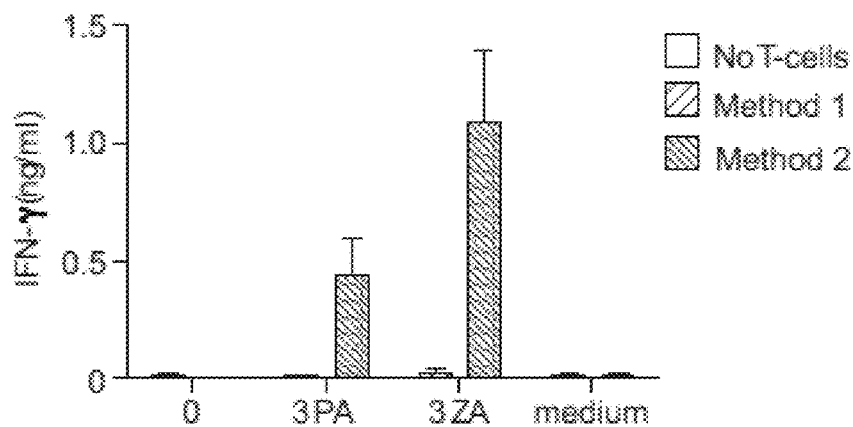
Figure 7N:
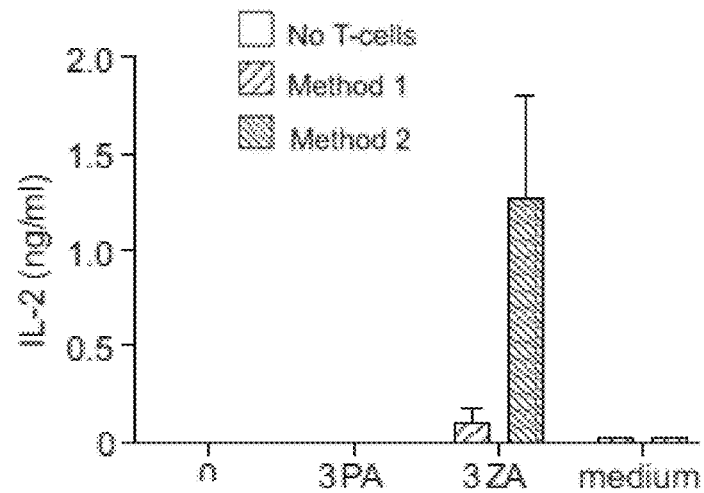
Figure 7O:
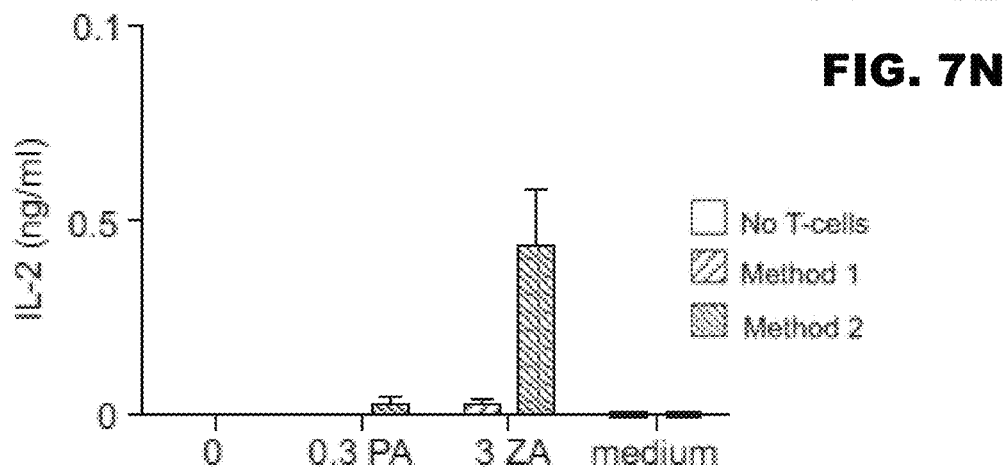

After expansion of γδ T-cells for 2 weeks using either method 1 or 2, co-cultures were established in triplicate at a 5:1 effector:target ratio in 96 well plates. Where indicated, tumor cells were pulsed for 24 h with the indicated concentration (μg/ml) of zoledronic (ZA) or pamidronic acid (PA), prior to addition of γδ T-cells. After a further 24 hours, supernatants were harvested and analysed for Interferon-γ or Interleukin-2 by ELISA. The results are shown in FIGS. 7A-O. Interferon (IFN)-γ production is shown for the following tumor cell monolayers: ovarian cancer cell lines FIG. 7(A) Kuramochi, FIG. 7(B) IGROV-1, FIG. 7(C) SKOV-3, FIG. 7(D) TOV-21G; breast cancer cell lines FIG. 7(E) MDA-MB-468; FIG. 7(F) MDA-MB-231; FIG. 7(G) BT-20; myeloid leukemic cell lines FIG. 7(H) U937, FIG. 7(I) KG-1. In addition, interleukin-2 production is shown for co-cultivation experiments undertaken with FIG. 7(J) Kuramochi, FIG. 7(K) U937, FIG. 7(L) KG-1, FIG. 7(M) MDA-MB-231, FIG. 7(N) MDA-MB-468 and FIG. 7(O) BT-20 tumor cells.

When compared to cells that had been expanded using method 1, method 2-expanded cells produced significantly higher levels of IFN-γ when engaging tumor cell targets. This effect was most pronounced when transformed cells had been pulsed with very low concentrations of NBP agents (FIGS. 7A-G). Method 2-expanded cells also produced IL-2 under these conditions, a finding that was not observed using method 1-expanded cells (FIGS. 7H-K).

Figure 8A:
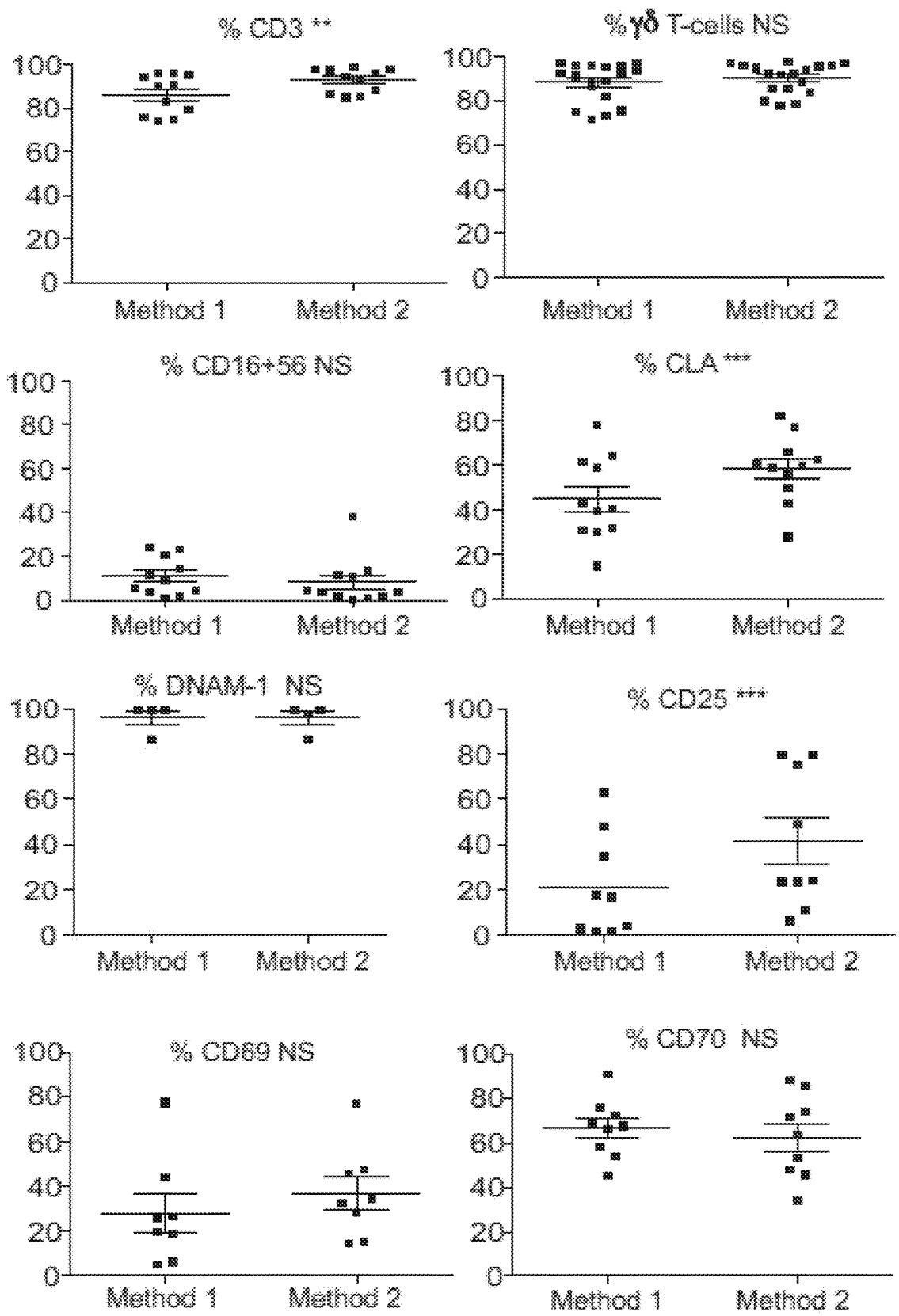
FIGS. 8A-C show the results of immunophenotypic analysis of method 1 and method 2-expanded Vγ9Vδ2 T-cells.
Figure 8A:
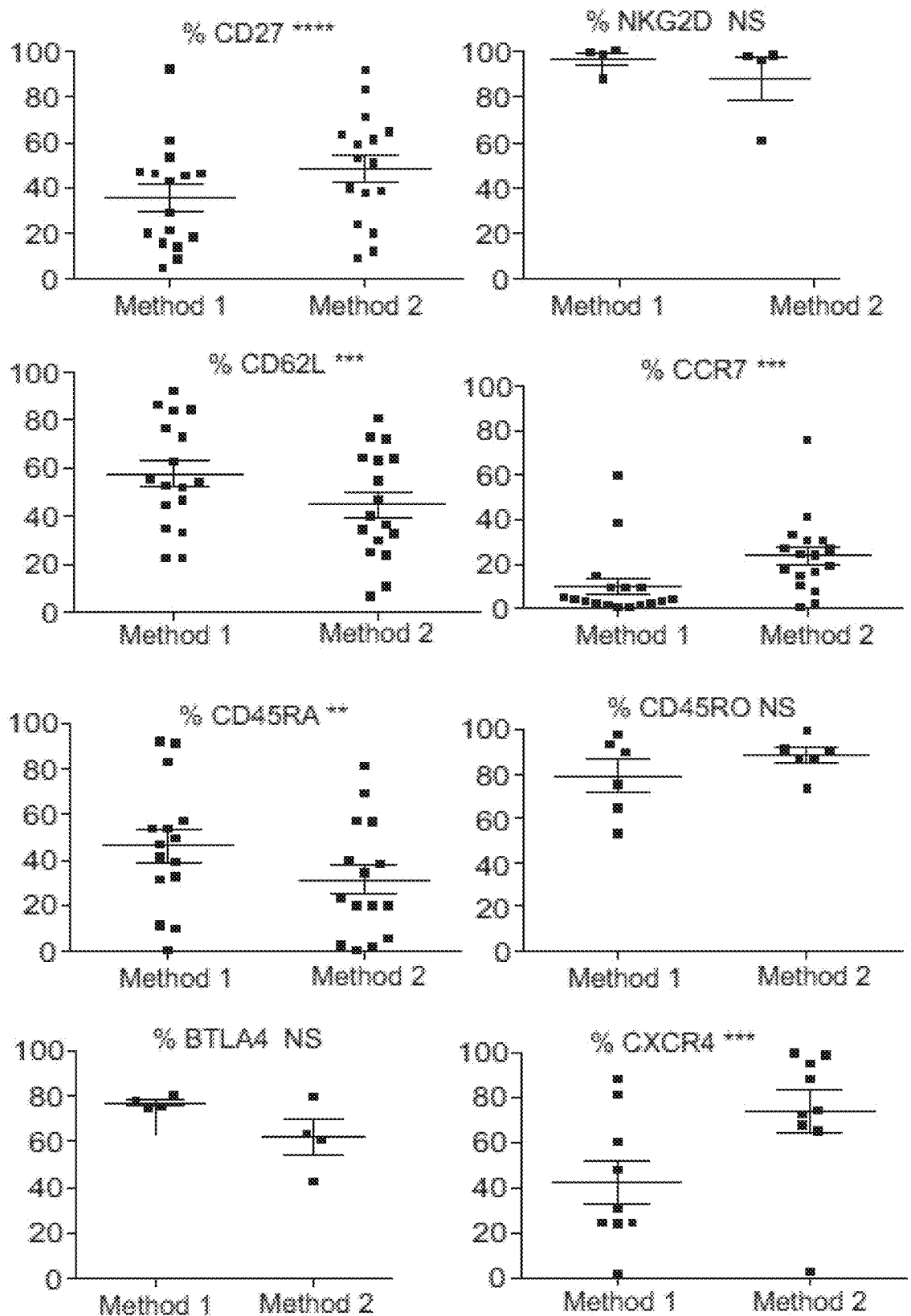
Figure 8A:
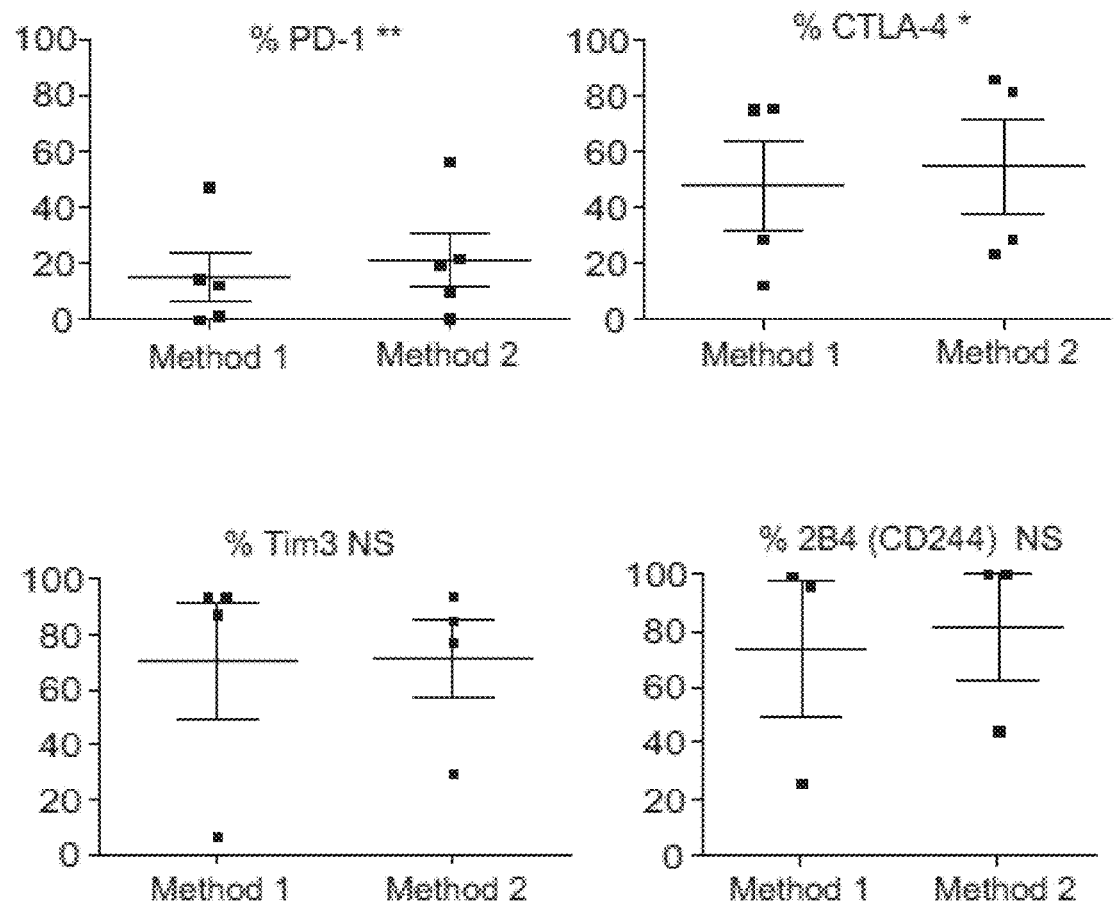
Figure 8B:
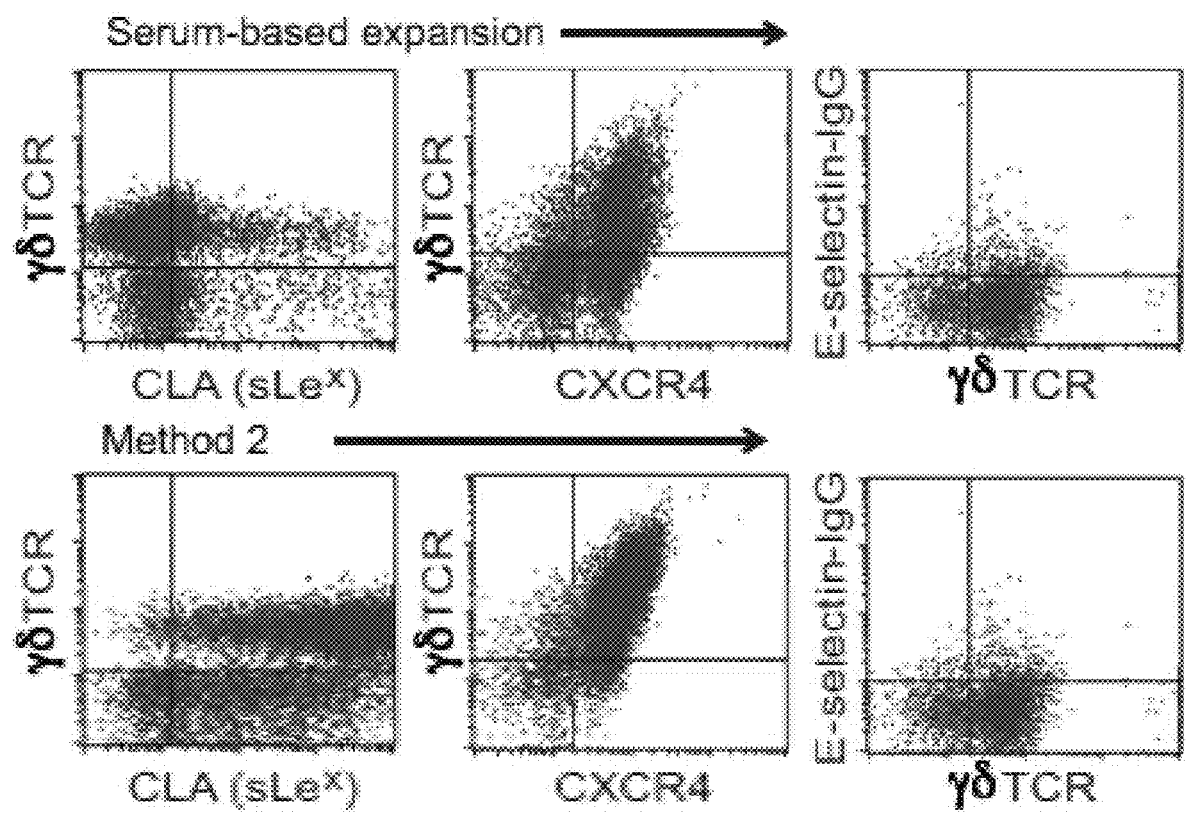
Figure 8C:
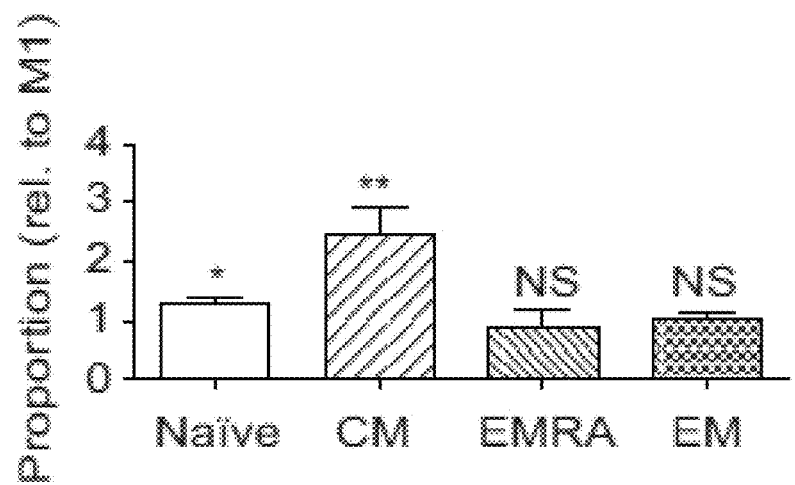

Finally, the phenotype of method 1 and method 2 cells was investigated using conventional methods and the results are illustrated in FIGS. 8A-C. Method 2-expanded cells were found to express a distinctive phenotype, with high levels of homing receptors (CXCR4, CLA, E-selectin binding activity) and memory markers (CD27, CD45RO). In addition, the proportion of naïve (CD45RA⁺ and CCR7⁺) and central memory (CD45 and CD27⁺) cells was higher in method 2 expanded cells as compared to method 1 expanded cells. Thus these cells are distinguishable from cells produced using other expansion protocols.

EXAMPLE 2

Alternative Cell Expansion Process

Figure 9A:
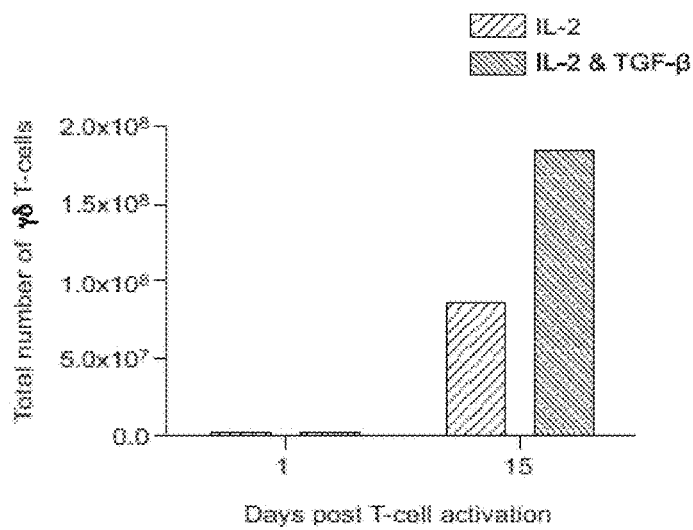
FIG. 9A shows an evaluation of cell number of γδ T-cells present in cultures obtained using method 1 and the method of the invention in a different basic medium (RPMI+10% human AB serum).
Figure 9B:
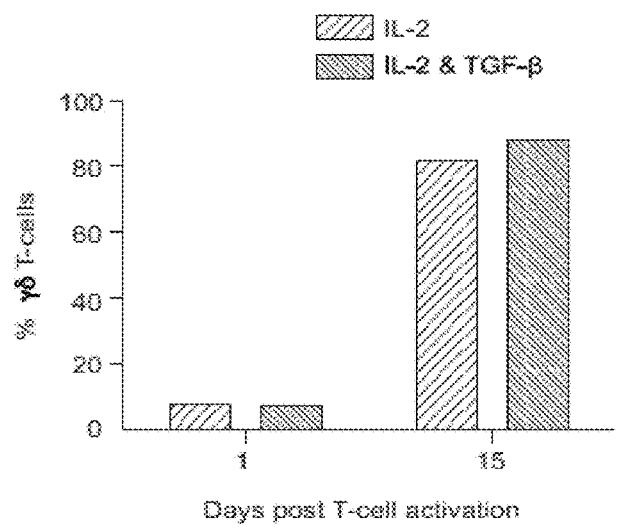
FIG. 9B shows the percentage of γδ T-cells present in cultures obtained using method 1 and the method of the invention in a different basic medium (RPMI+10% human AB serum).

The methodology of Example 1 above was repeated using a different basic medium, specifically RPMI+human AB serum. In particular, PBMC (3×10⁶ cells/ml) were cultured in RPMI+10% human AB serum containing zoledronic acid (1 μg/ml)+IL-2 (100 U/ml; method 1) or zoledronic acid (1 μg/ml)+IL-2 (100 U/ml)+TGF-β (5 ng/ml; method 2). Cell number was evaluated on day 15 and the results are shown in FIG. 9A. The percentage of γδ T-cells present in each culture was evaluated on the day of initiation of the cultures (day 1) and after a further 14 days (day 15) and the results are shown in FIG. 9B.

As before, it is clear that the addition of TGF-β has enhanced cell expansion.

EXAMPLE 3

In-Vivo Therapeutic Activity

In addition, the in-vivo therapeutic activity of expanded Vγ9Vδ2 T-cells against an established burden of malignant disease were compared. Twenty SCID Beige mice were inoculated with 1×10⁶ firefly luciferase-expressing U937 leukemic cells by tail vein injection and were then divided into 4 groups of 5 mice each. After 4 days, mice were treated as follows: Group 1 is a control group that received PBS alone. Group 2 received pamidronic acid (200 μg IV) alone. Group 3 received pamidronic acid (200 μg IV on day 4) followed by 20×10⁶ (day 5) and 10×10⁶ (day 6) Vγ9Vδ2 T-cells that had been expanded using method 1 (IV). Group 4 received pamidronic acid (200 μg IV on day 4) followed by 20×10⁶ (day 5) and 10×10⁶ (day 6) Vγ9Vδ2 T-cells that had been expanded using method 2 (administered IV). Leukemic burden was monitored thereafter by serial bioluminescence imaging.

The results are shown in FIG. 10. It is clear that the efficacy of the cells obtained by method 2 of the invention is significantly greater in this assay.

EXAMPLE 4

In-Vivo Activity of Cells of the Invention in Conjunction with IL-2

In a separate experiment, the in-vivo therapeutic activity of intravenously administered expanded Vγ9Vδ2 T-cells obtained using the method of the invention (M2) against an established burden of malignant disease (U937 leukemia) in SCID Beige mice was measured. Mice were divided into 4 groups of 5 mice and each received 1 million U937 cells IV on day 1. Thereafter, one group received treatment that may be summarised as follows:

| Group | Treatment |
|---|---|
| 1 | PBS (control) |
| 2 | Zoledronic acid + IL-2 |
| 3 | M2 + IL-2 |
| 4 | M2 + IL-2 + Zoledronic acid |

Where administered, 20 µg Zoledronic acid was administered intravenously 24 hours after treatment with U937 cells. Mice receiving M2 cells were given 2 treatments of 15 million γδ T-cells intravenously, one day later. Those receiving IL-2 were given 10,000 U of IL-2 by the intraperitoneal (IP) route at the same time as M2 administration. On the following 2 days, mice received 10,000 U IL-2 IP. A control group received phosphate-buffered saline (PBS) alone.

Figure 11A:
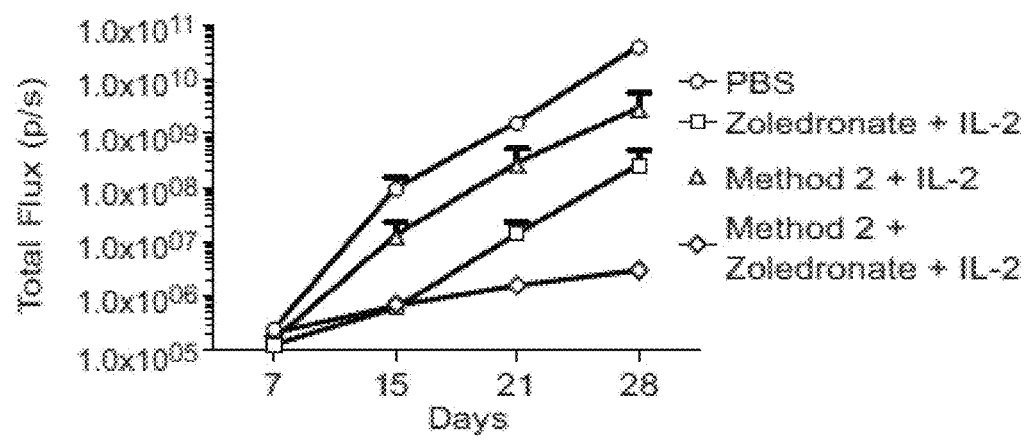
FIGS. 11A-B show the in-vivo therapeutic activity of intravenously administered expanded Vγ9Vδ2 T-cells obtained using the method of the invention against an established burden of malignant disease (U937 leukemia) in SCID Beige mice where

Bioluminescence from the malignant cells was measured on days 7, 15, 21 and 28 as an indicator of tumor burden. The results are shown in FIG. 11A. The results show that Vγ9Vδ2 T-cells obtained using the method of the invention significantly reduce tumor burden, in particular when administered with an activator.

Figure 11B:
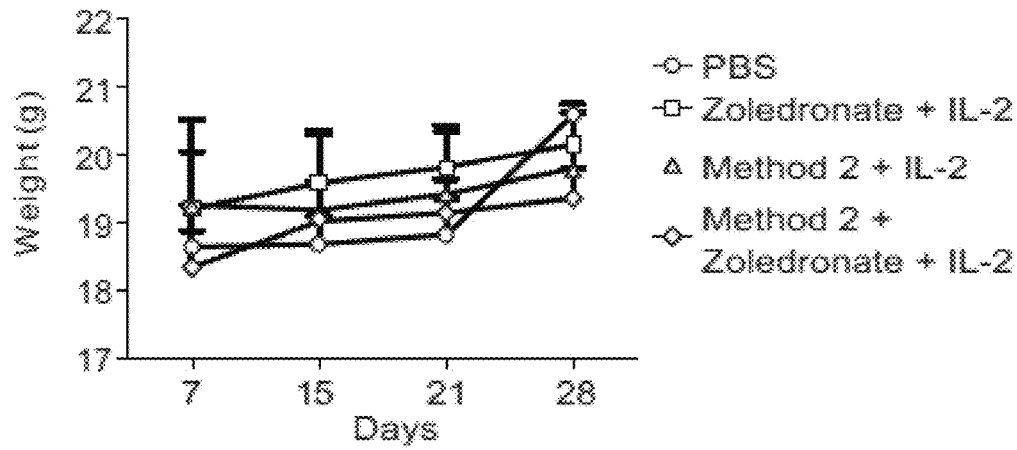

Mice were weighed over the course of the treatment to provide an indication of the toxicity of the treatment. The results, shown in FIG. 11B, indicate that that there is no significant toxicity associated with the treatment.

EXAMPLE 5

In-Vivo Therapeutic Effect Against Breast Cancer

In this experiment, 20 SCID Beige mice having an established burden of malignant disease in the form of MDA-MB-231 triple negative breast cancer, implanted in the mammary fat pad of the mice, were used. Again, mice were divided into four groups for treatment. Mice were treated as follows: Group 1 is a control group that received PBS alone. Group 2 received 20 µg Zoledronic acid intravenously. Group 3 received 20×10$^6$ (day 2) and 10×10$^6$ (day 3) Vγ9Vδ2 T-cells that had been expanded using method 2 intravenously. Group 4 received 20 µg Zoledronic acid intravenously on day 1 followed by 20×10$^6$ (day 2) and 10×10$^6$ (day 2) Vγ9Vδ2 T-cells that had been expanded using method 2.

Figure 12A:
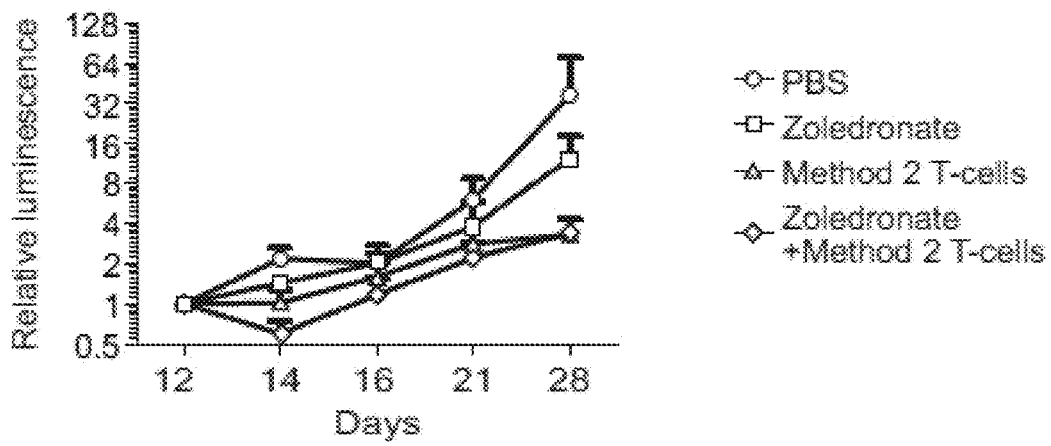
FIGS. 12A-C show the in-vivo therapeutic activity of intravenously administered expanded Vγ9Vδ2 T-cells obtained using method 2 against an established burden of malignant disease (MDA-MB-231 triple negative breast cancer, implanted in the mammary fat pad of SCID Beige mice).
Figure 12B:
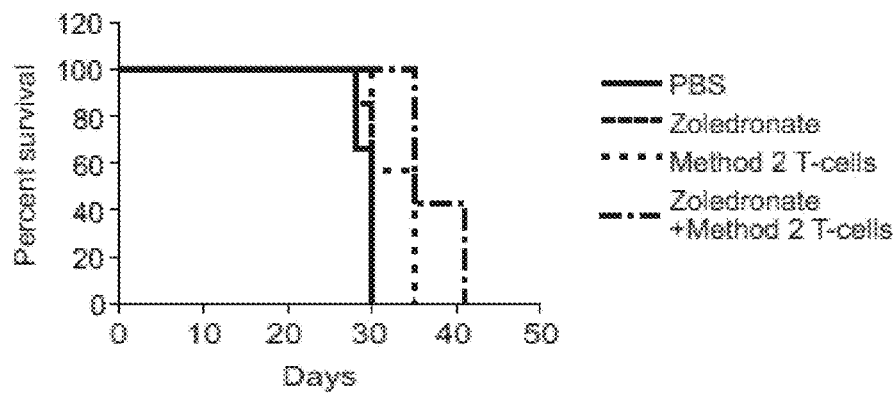
Figure 12C:
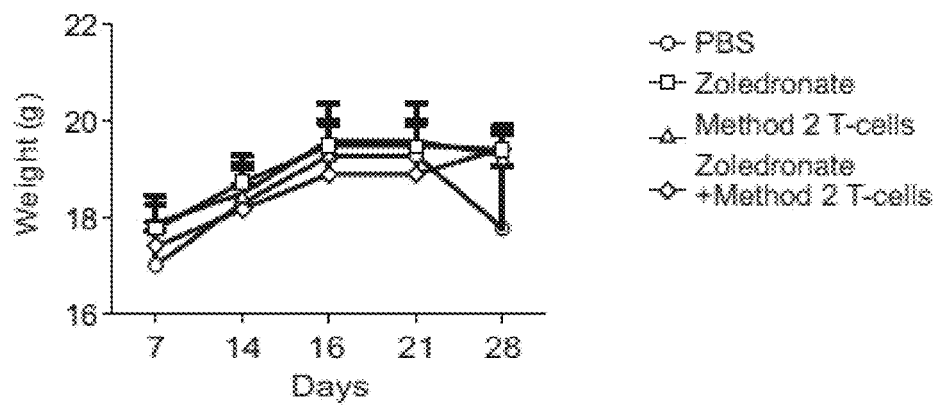

The resultant tumor burden as measured by bioluminesence was measured over a period of 28 days. The results are shown in FIG. 12. In this case, the cells obtained using the method of the invention produced a significant reduction in tumor burden (FIG. 12A) accompanied by prolonged survival (FIG. 12B).

Mice were weighed over the course of the treatment to provide an indication of the toxicity of the treatment. The results, shown in FIG. 12C, indicate that that there is no significant toxicity associated with the treatment.

EXAMPLE 6

Purification of Expanded γδ T-Cells

Figure 13A:
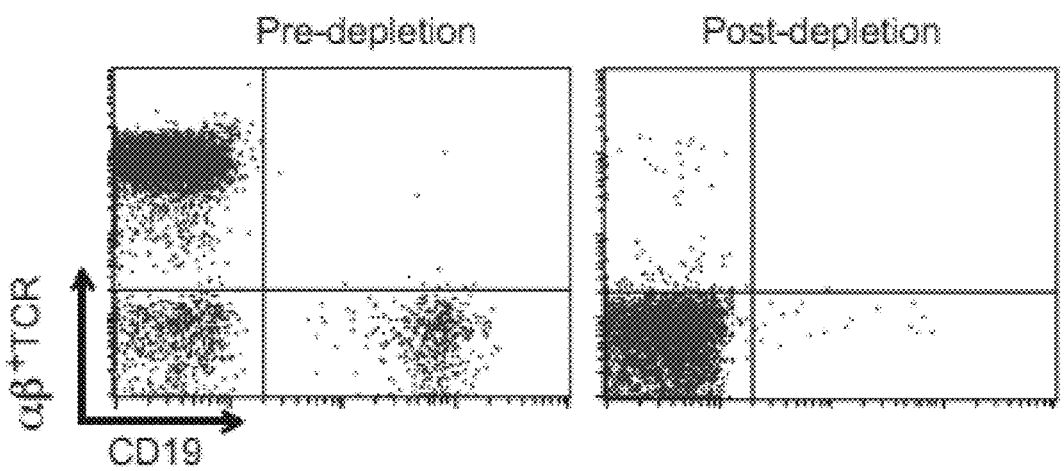
FIGS. 13A-H show the results of the use of various purification methods, where

In a first experiment, Vγ9Vδ2 T-cells were purified from freshly isolated PBMC by negative selection using a CD19 and/or a αβ T-cell microbead isolation kit. Where both kits were used, residual contaminating CD19 and αβ T-cells were <0.1% as shown in FIG. 13(A).

Figure 13B:
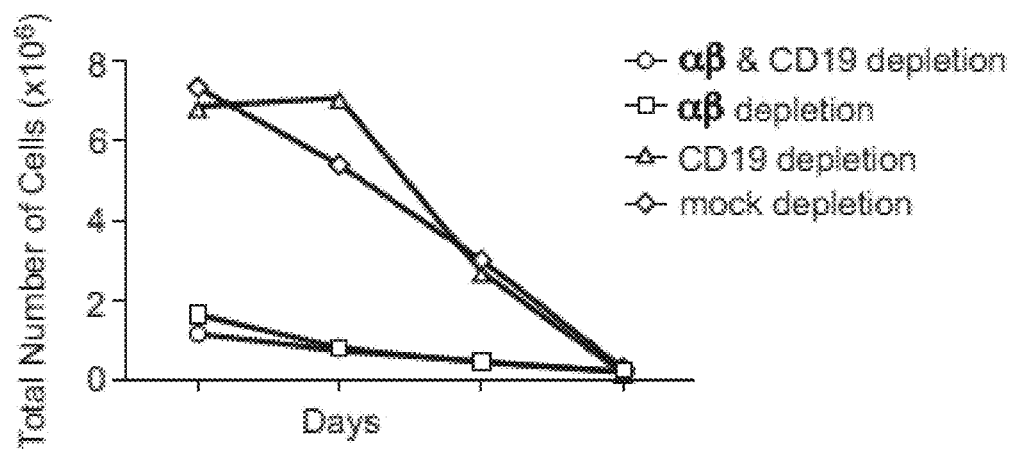

The purified cells were subjected to expansion using method 2 as described in Example 1. However, these cells were not able to expand as illustrated in FIG. 13(B). Thus it appears that the starting material must comprise PBMCs.

Figure 13C:
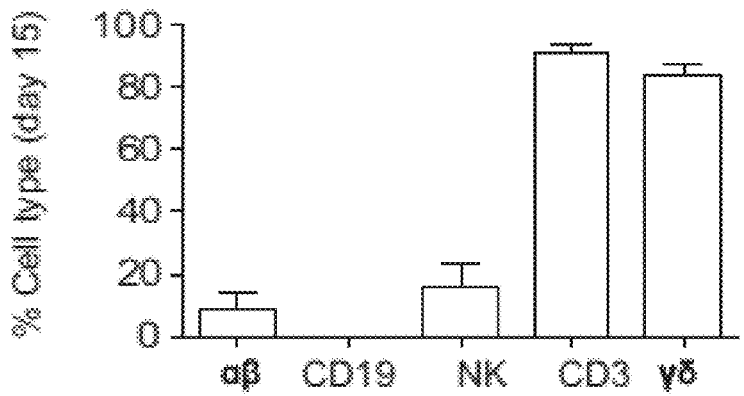

In other experiments, γδ T-cells were expanded from PBMCs using method 2 for 15 days. At this point, flow cytometry analysis demonstrated that significant numbers of αβ T-cells remain, accompanied by small numbers of CD19$^+$ cells (n=4) (FIG. 13(C)).

Figure 13D:
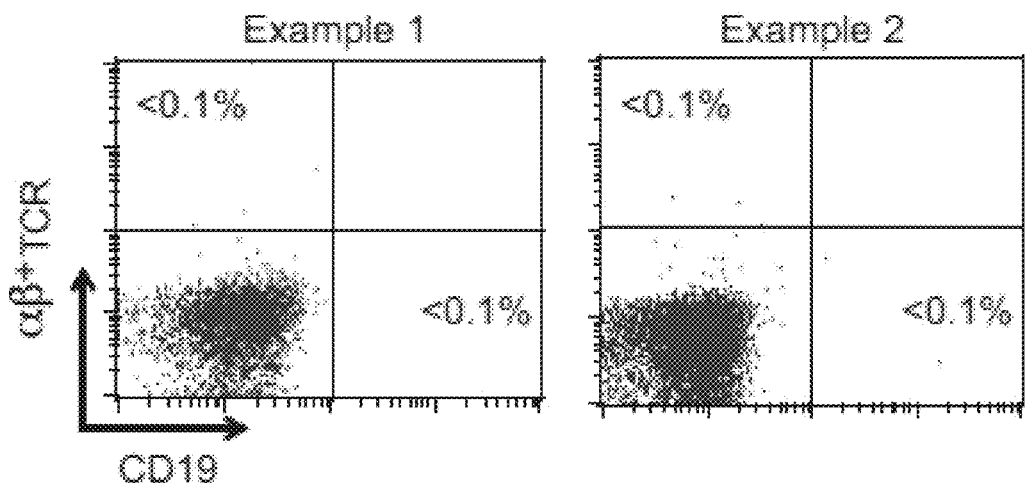

The resultant product was then depleted of CD19 and αβ T-cells by negative selection, as described above in relation to FIG. 13(A). Two representative flow cytometric analyses are shown in FIG. 13(D) to indicate the efficiency of the depletion process.

Figure 13E:
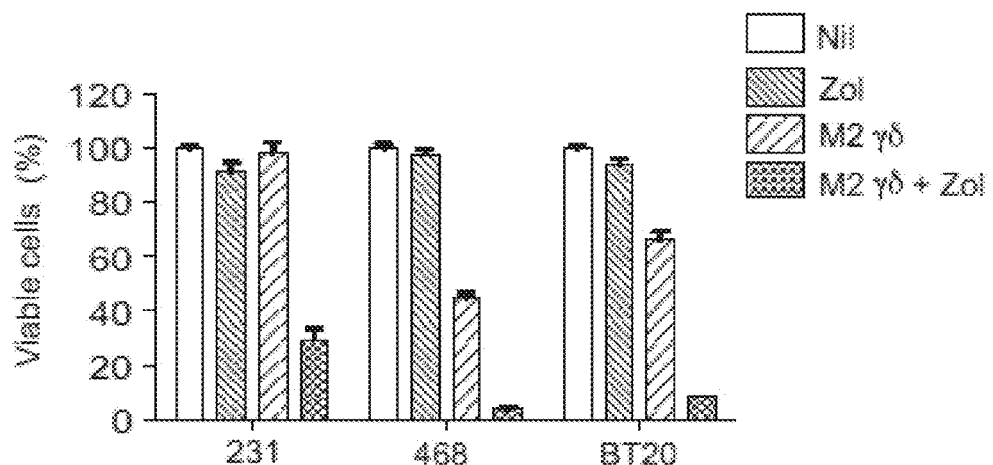
Figure 13F:
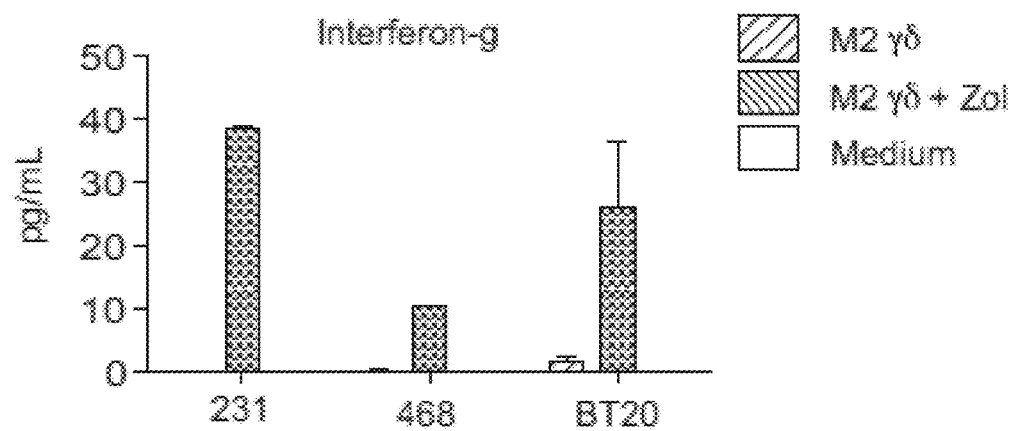
Figure 13F:
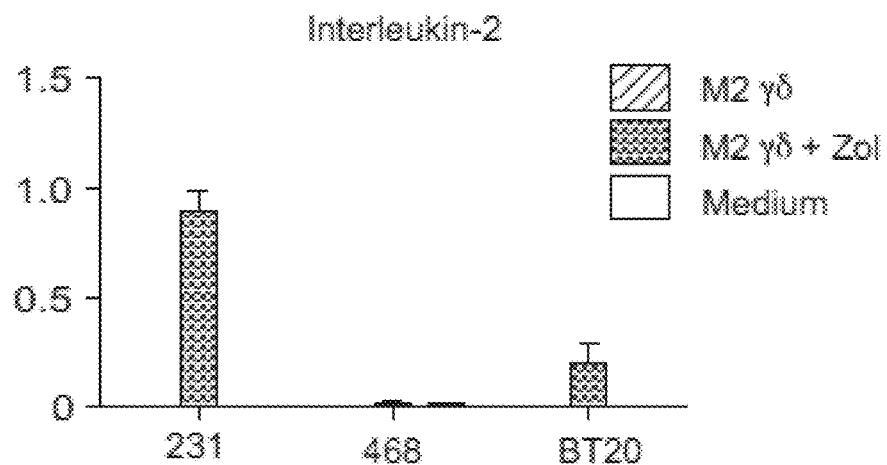

Following purification by negative selection using the MACS beads (Miltenyi), method 2-expanded γδ T-cells were tested in a 24 hour cytotoxicity assay (5:1 effector: target ratio) against MDA-MB-231, MDA-MB-468 or BT20 triple negative tumor cells or U937 or KG-1 myeloid leukemic cells using methodology similar to that described in Example 1. Cells were tested alone, or in combination with zoledronic acid. There was a negative control and a control with activator alone. Tumor cell viability was measured by luciferase assay and/or MTT assay (n=2). The results are shown in FIG. 13(E) and FIG. 13(F) respectively. As is clear, the combination of T cells and activator produced a significant reduction in tumor cell viability.

Figure 13G:
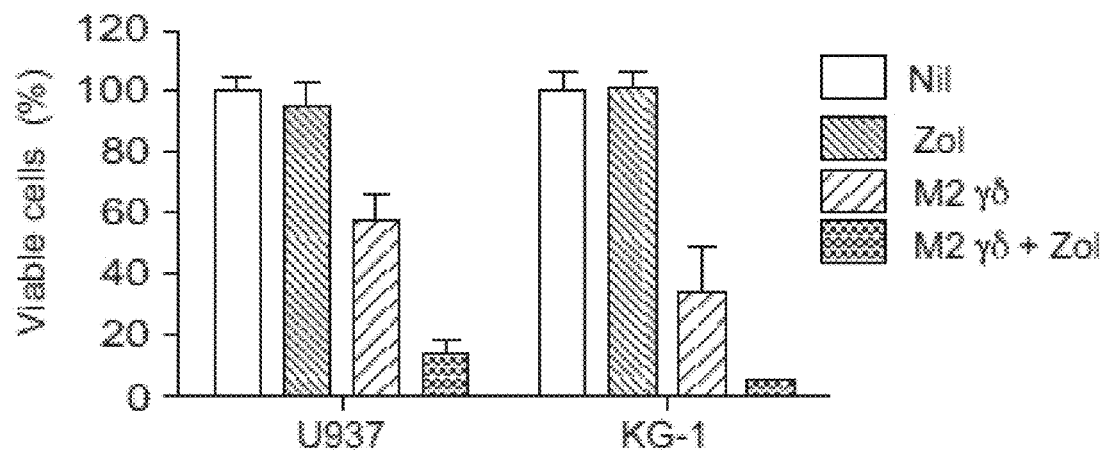
Figure 13H:
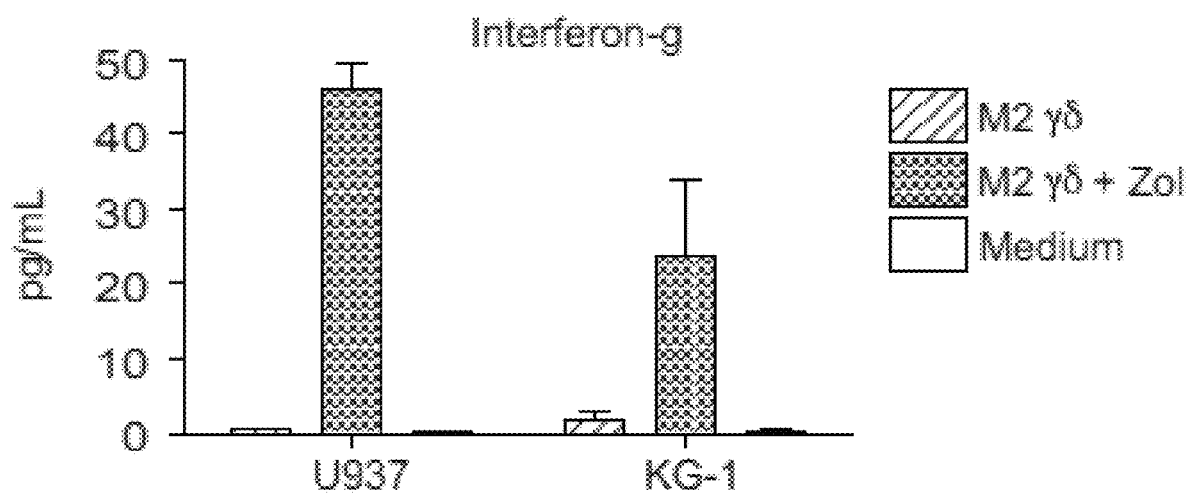

Supernatants were harvested from these breast cancer and leukemia co-cultures, after 24 h, and analysed for the presence of IFN-γ and/or IL-2. The results are shown in FIGS. 13(G) and 13(H) respectively. Cytokine levels were substantially raised in the case of the combination of T-cells expanded in accordance with the invention and activator.

These experiments show that method 2 expanded γδ T-cells are fully functional if purified by negative selection after expansion, but not before. This purification facilitates the safe allogeneic use of these cells since potentially hazardous B-cells (CD19$^+$) and αβ T-cells have been removed.

EXAMPLE 7

Genetic Engineering of Expanded Cells

To further confirm the functionality of γδ T-cells expanded in accordance with the invention, they were genetically engineered by retroviral transduction. Cells were either transduced by pre-loading viral vector onto a RetroNectin coated solid phase or by addition of viral supernatant to the expanding cells.

Figure 14A:
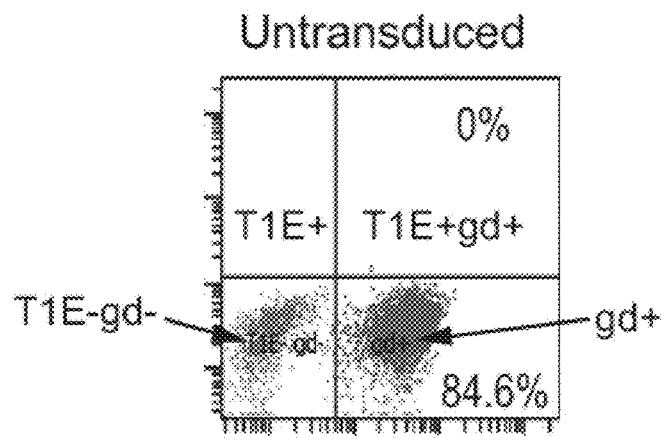
FIGS. 14A-C show that the flow cytometry results of genetically engineered γδ T-cells obtained using the method of the invention, using a technique in which viral vector was pre-loaded onto a RetroNectin coated solid phase FIG. 14(B), or by addition of viral supernatant to cells FIG. 14(C), as compared to untransduced controls FIG. 14(A).
Figure 14B:
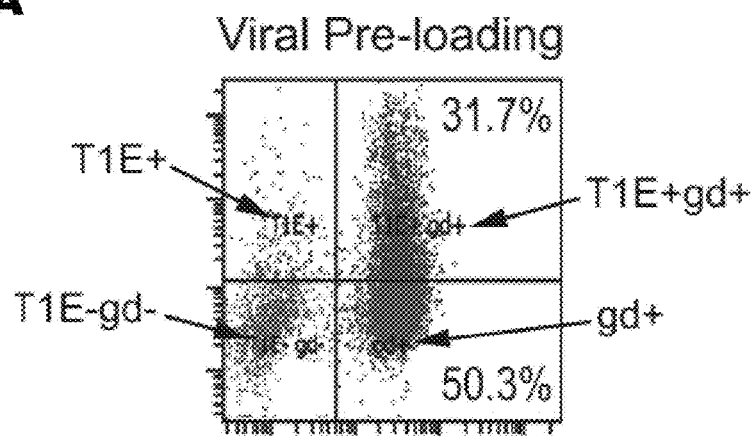
Figure 14C:
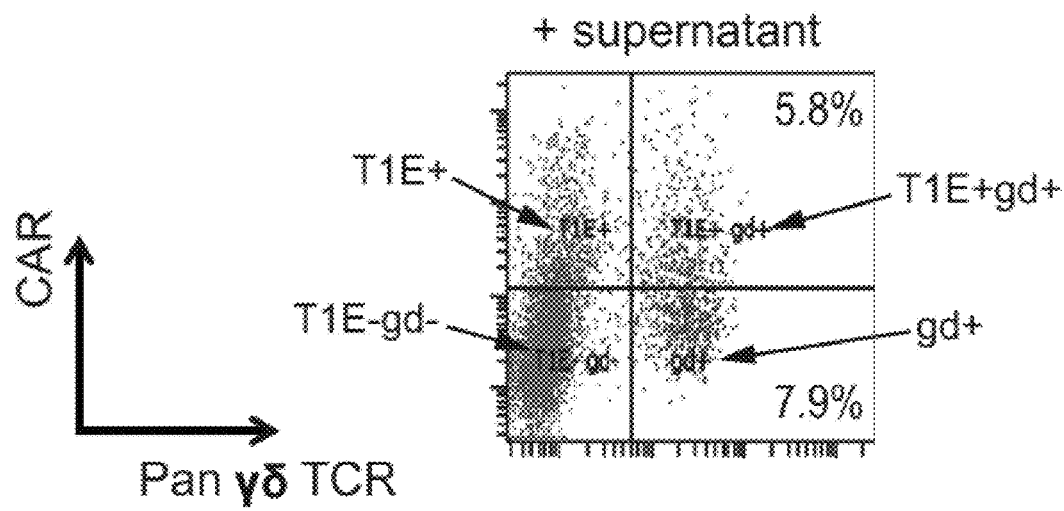

It was clear that in order to preserve the efficient enrichment of these cells during expansion, it is preferable to pre-load viral vector onto a RetroNectin coated solid phase (FIG. 14(B)), rather than addition of viral supernatant (FIG. 14(C)). This is indicated by the greater percentage of transduced cells and the greater percentage of γδ T-cells present when gene transfer is achieved using the pre-loading method.

EXAMPLE 8

Effects of Combination of γδ T-Cells with Chemotherapeutic Agent

Cytotoxicity assays were established in triplicate at a 1:1 effector:target ratio in 96 well plates containing either U937 tumor cells or KG-1 tumor cells. Where indicated, tumor cells were pulsed for 24 h with the indicated concentrations of cytarabine, prior to addition of γδ T-cells, produced either using the method of the invention (M2) or the method of the comparative example (M1) above. There were three donors for the M2 cells and two donors for the M1 cells. A control group received no cytarabine.

Figure 15A:
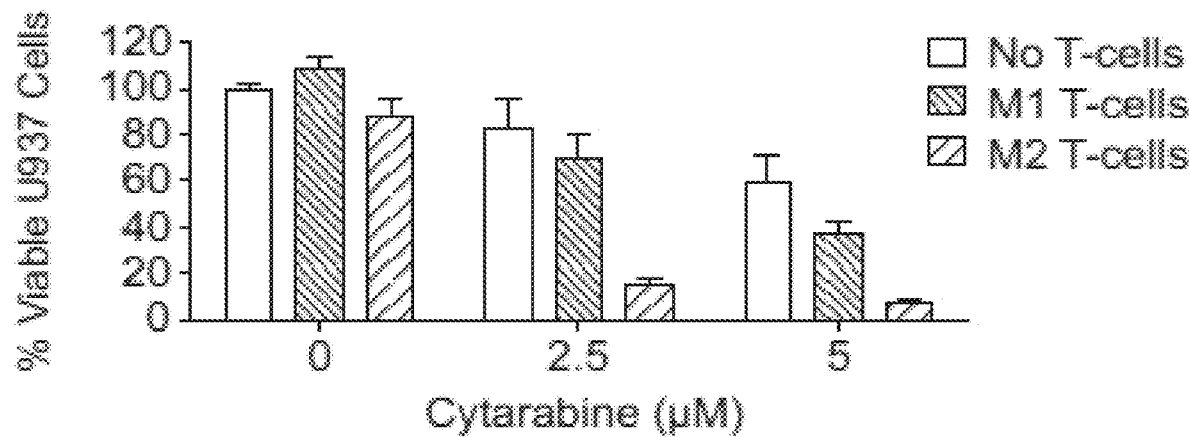
FIGS. 15A-B show the results of in-vitro cytoxicity assays against tumor cells (FIG. 15(A) U937 cells and FIG. 15(B) KG1 cells) when treated with the chemotherapeutic agent, cytarabine, at various concentrations for 24 hours preceding the addition of γδ T-cells, including some obtained using the method of the invention (M2).
Figure 15B:
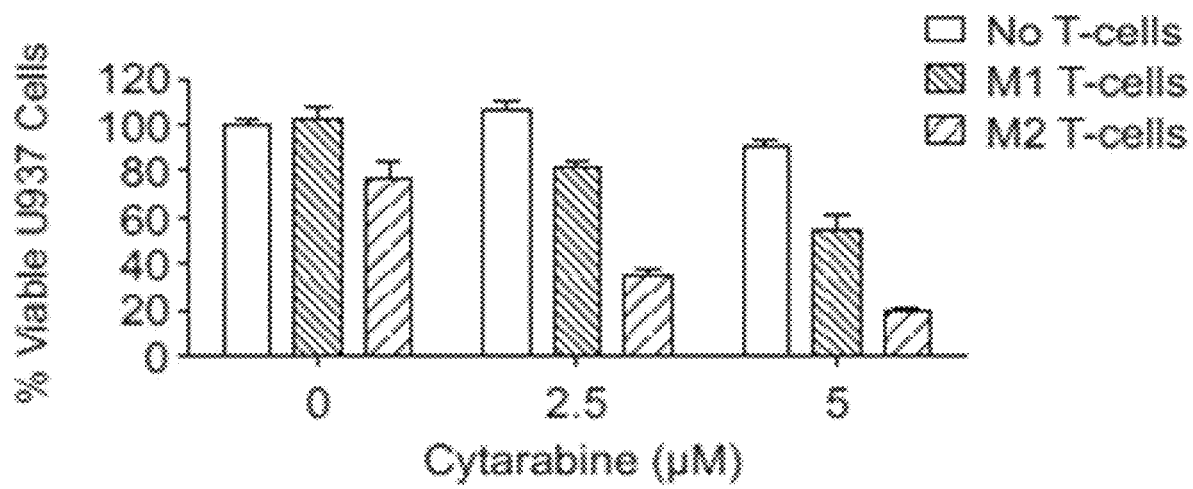

Residual tumor cell viability was measured after overnight co-culture with Vγ9Vδ2 T-cells by luciferase assay. The results, shown in FIGS. 15A-B show that sub-lethal doses of cytarabine potentiated the anti-tumor activity of Vγ9Vδ2 T-cells expanded using method 2 against two cell models of AML (three donors for M2 cells and two donors for M1 cells)

In a separate experiment, fifteen SCID Beige mice were inoculated with $1 \times 10^6$ firefly luciferase-expressing U937 leukemic cells by tail vein injection and were then divided into 3 groups of 5 mice each. After 4 days, mice were treated as follows: Group 1 is a control group that received PBS alone. Group 2 received cytarabine (480 mg/Kg IV on day 4) and IL-2 (10000 IP on day 5, 6, 7 and 8). Group 3 received cytarabine (480 mg/Kg IV on day 4) followed by $20 \times 10^6$ (day 5 and 6) Vγ9Vδ2 that had been expanded using method 2 (IV) and IL-2 (10000 IP at days 5, 6, 7 and 8).

Figure 16A:
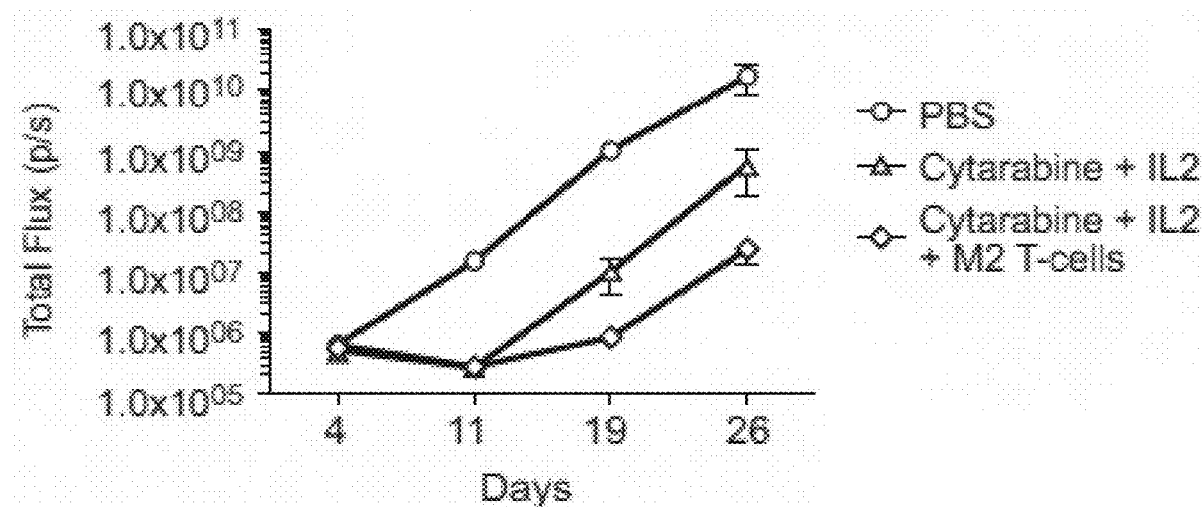
FIGS. 16A-B are a set of graphs showing the results of in-vivo tests in which γδ T-cells of the invention are administered in combination with cyatarabine and IL-2, as compared to the use of cyatarabine and IL-2 alone where
Figure 16B:
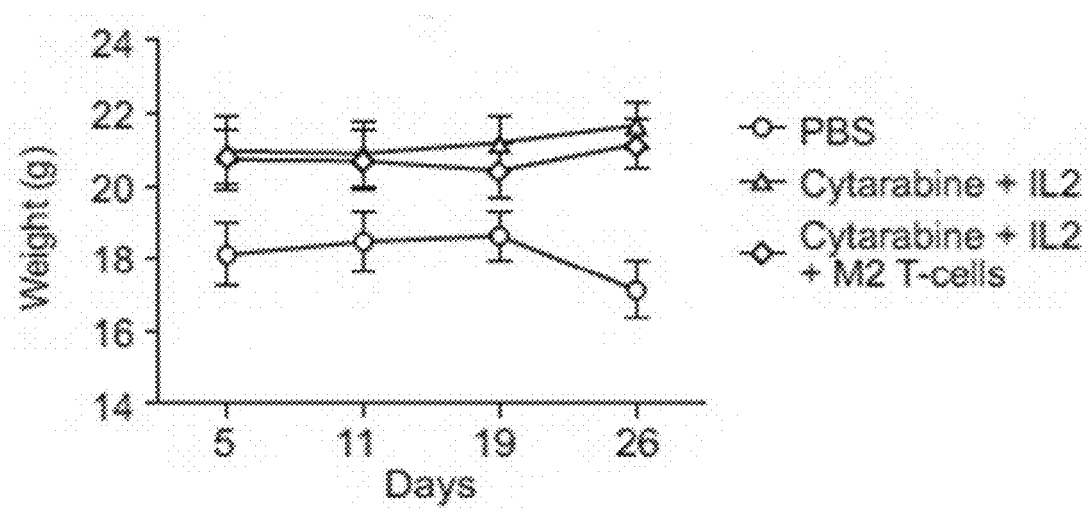

Leukemic burden was monitored thereafter by serial bioluminescence imaging. Bioluminescence from the malignant cells was measured on days 4, 11, 19 and 26 as an indicator of tumor burden. The results are shown in FIG. 16(A) and indicate that Vγ9Vδ2 T-cells obtained using the method of the invention reduce tumor burden most effectively when administered with cytarabine. Mice were weighed over the course of the treatment to provide an indication of the toxicity of the treatment. The results shown in FIG. 16(B), indicate that that there is no significant toxicity associated with the treatment.

REFERENCES

[1] P. Vantourout et al., Nat Rev Immunol, 13 (2013) 88-100.
[2] P. Vantourout et al., Sci Transl Med, 6 (2014) 231ra249.
[3] M. Brandes et al., Science, 309 (2005) 264-268.
[4] M. Wilhelm et al., J Transl Med, 12 (2014) 45.
[5] I. Benzaid et al., Cancer Res, 71 (2011) 4562-4572.
[6] J. W. Clendening et al., Proc Natl Acad Sci USA, 107 (2010) 15051-15056.
[7] U. Laggner et al., Clin Immunol, 131 (2009) 367-373.
[8] J. E. Dunford et al., J Med Chem, 51 (2008) 2187-2195.
[9] I. Benzaid et al., Clin Cancer Res, 18 (2012) 6249-6259.
[10] F. Dieli et al., Cancer Res, 67 (2007) 7450-7457.
[11] J. Bennouna et al., Cancer Immunol Immunother, 57 (2008) 1599-1609.
[12] H. Kobayashi et al., Anticancer Res, 30 (2010) 575-579.
[13] A. J. Nicol et al., Br J Cancer, 105 (2011) 778-786.
[14] Y. Gu et al., J Immunol Methods, 402 (2014) 82-87.
[15] R. Casetti et al., J Immunol, 183 (2009) 3574-3577.
[16] A. C. Parente-Pereira et al., J Immunol, 193 (2014) 5557-5566.
[17] A. C. Parente-Pereira et al., J Biol Methods, 1 (2014) e7.
[18] S. R. Mattarollo et al., Cancer Immunol. Immunother. (2007) 56:1285-1297

The invention claimed is:

1. A method for expanding a population of effector γδ T-cells, said method comprising culturing isolated Peripheral Blood Mononuclear Cells (PBMCs) in a medium comprising (i) transforming growth factor beta (TGF-β), (ii) interleukin-2 (IL-2), and (iii) an activator for Vγ9Vδ2 T-cells,
   wherein the medium is serum free.
2. The method of claim 1 wherein no additional cytokines are present in the medium.
3. The method of claim 1 wherein the activator is an aminobisphosphonate.
4. The method of claim 1 wherein the PBMCs are human PBMCs.
5. The method of claim 4 wherein the PBMCs are from a healthy human.
6. The method of claim 1 wherein CD19 B cells and/or αβ T-cells are removed from the expanded product.
7. The method of claim 3 wherein the aminobisphosphonate is zoledronic acid, alendronic acid, pamidronic acid, ibandronic acid, or a salt thereof.
8. The method of claim 7 wherein the aminobisphosphonate is zoledronic acid or a salt thereof.
9. The method of claim 4 wherein the effector γδ T-cells are human Vγ9Vδ2 T-cells.
10. The method of claim 4 wherein the PBMCs are from a human patient.
11. The method of claim 2 wherein the activator is an aminobisphosphonate.
12. The method of claim 2 wherein the PBMCs are human PBMCs.
13. The method of claim 12 wherein the PBMCs are from a healthy human.
14. The method of claim 2 wherein CD19 B cells and/or αβ T-cells are removed from the expanded product.
15. The method of claim 11 wherein the aminobisphosphonate is zoledronic acid, alendronic acid, pamidronic acid, ibandronic acid, or a salt thereof.
16. The method of claim 15 wherein the aminobisphosphonate is zoledronic acid or a salt thereof.

* * * * *